(12) United States Patent
Jessen et al.

(10) Patent No.: US 10,839,937 B1
(45) Date of Patent: Nov. 17, 2020

(54) WHOLE CELL CIRCULAR DELTA VIEWER AND NAVIGATOR

(71) Applicant: X Development LLC, Mountain View, CA (US)

(72) Inventors: Johan Jessen, San Francisco, CA (US); Ivan Grubisic, Oakland, CA (US); Matthew Sibigtroth, Richmond, CA (US)

(73) Assignee: X DEVELOPMENT LLC, Mountain View, CA (US)

( * ) Notice: Subject to any disclaimer, the term of this patent is extended or adjusted under 35 U.S.C. 154(b) by 175 days.

(21) Appl. No.: 16/039,546

(22) Filed: Jul. 19, 2018

(51) Int. Cl.
| | | |
|---|---|---|
| *G16B 5/00* | (2019.01) | |
| *G16B 30/00* | (2019.01) | |
| *G06F 3/0481* | (2013.01) | |
| *G06F 3/0484* | (2013.01) | |
| *G16B 45/00* | (2019.01) | |

(52) U.S. Cl.
CPC .............. *G16B 5/00* (2019.02); *G06F 3/0481* (2013.01); *G06F 3/04847* (2013.01); *G16B 45/00* (2019.02); *G16B 30/00* (2019.02)

(58) Field of Classification Search
CPC .......... G16B 30/00; G16B 5/00; G16B 45/00; G06F 3/0481; G06F 3/04847
See application file for complete search history.

(56) References Cited

U.S. PATENT DOCUMENTS

| | | | |
|---|---|---|---|
| 2011/0219324 A1* | 9/2011 | Watanabe | G06F 3/048 715/771 |
| 2011/0289459 A1* | 11/2011 | Athans | G06F 3/0481 715/854 |
| 2016/0019668 A1* | 1/2016 | Kilinski | G06Q 10/0635 705/325 |

(Continued)

FOREIGN PATENT DOCUMENTS

WO    WO 2014/015196 A2    1/2014

OTHER PUBLICATIONS

"Non-Coding RNA Analysis" p. 16 <https://currentprotocols.onlinelibrary.wiley.com/doi/full/10.1002/cpbi.51> (Year: 2018).*

(Continued)

*Primary Examiner* — Beau D Spratt
(74) *Attorney, Agent, or Firm* — Kilpatrick Townsend & Stockton LLP

(57) ABSTRACT

After running a simulation on a biological cell, a simulation system displays a circular viewer for presenting simulation data. The circular viewer is a graphical element which contains a plurality of circular graphical elements, wherein each circular graphical element displays simulation data of one biological category ordered around the circular graphical element. Responsive to a user input, the circular viewer updates the circular graphical elements to visually indicate subsets of simulation data in each graphical element that are above a threshold differential from a baseline cell state of the biological cell. The circular viewer may additionally display (Continued)

connectors linking portions of simulation data from different circular graphical elements. Moreover, the circular viewer may update to display simulation data in the circular graphical elements over a plurality of time steps over which the simulation has occurred.

18 Claims, 25 Drawing Sheets

(56) References Cited

U.S. PATENT DOCUMENTS

| | | | | |
|---|---|---|---|---|
| 2017/0016008 | A1* | 1/2017 | Sharma | C12N 15/67 |
| 2018/0196914 | A1* | 7/2018 | Ejtehadi | G16B 5/00 |
| 2018/0365375 | A1* | 12/2018 | Flygare | G16B 40/00 |
| 2019/0136229 | A1* | 5/2019 | Josephs | G16B 25/00 |
| 2019/0269743 | A1* | 9/2019 | Toledo | A61K 35/741 |

OTHER PUBLICATIONS

"Qiagen Bioinformatics Manuals" <http://resources.qiagenbioinformatics.com/manuals/clcmgm/current/index.php?manual=Visualization_OTU_abundance_tables.html> (Year: 2018).*

* cited by examiner

Outcome Type Bar
930

Data Interaction Menu
1410

| Gene | Enzyme |
|---|---|
| glk | glucokinase |

Page Title
1420

Summary

The cytoplasmic glucokinase is not required for growth on glucose as the carbon source, because glucose is phosphorylated during transport by the PTS system. Glucokinase phosphorylates glucose which is produced by amylomaltase.

Growth on glucose reduces the expression of glk by 50%. Growth on other carbon sources does not appear to affect glk expression [Meye97]. Overexpression of foreign proteins appears to induce expression of glk as well [Oh00a].

A crystal structure of the enzyme from E. coli O157:H7 has been reported [Lunin04]. Evolutionary relationships between glucose kinases based on their tertiary structures have been discussed [Kawai05].

A periplasmic glucokinase whose expression is induced during overexpression of foreign proteins has Interactional Panels
1430

Chemical process glucose + ATP →(glucokinase)→ glucose 6-phosphate + ADP

GCK Enzyme

FIG. 14B

WHOLE CELL CIRCULAR DELTA VIEWER AND NAVIGATOR

BACKGROUND

Field of Art

This disclosure generally relates to a simulation system of cell processes displaying simulation data of different cell reaction networks.

Description of the Related Art

A simulation system may perform an experiment which runs one or more simulations on a model system of a cell. Simulation parameters may include reactants, amount of reactants, gene mutation, gene knockout, timing, availability of enzymes, etc. The result of each simulation is simulation data which describes the cell's state throughout the simulation. The model cell's state may comprise amount of molecules, reaction rates, and so on.

A challenge arises in displaying all the simulation data for a user in an efficient fashion. At each stage of the simulation, the simulation system may keep counts of intermediary reactants, products, reactant rates, etc. Visualizing and presenting all simulation data for all the can be overwhelming. Still more challenging is presenting simulation data of significance to a user of the simulation system. Likewise there is a challenge of presenting items of the simulations which might be correlative, such as related reactions, related reactants, related products, etc. Another challenge might arise when the user attempts to compare different simulations against one another as the amount of data grows multiplicatively.

SUMMARY

A circular multi-viewer for presentation of the simulation data of a biological cell's processes. After running a simulation with the simulation system on the biological cell's processes, the simulation system has simulation data that may be compared to a baseline cell state of the biological cell's processes. The simulation data may be partitioned into many biological categories such as DNA replication, RNA transcription, protein translation, metabolism, cell wall transport, etc. The circular viewer is a graphical element of the GUI which presents the simulation data in circular graphical elements, wherein each circular graphical element may correspond to simulation data from one of many biological categories. The simulation data in each circular graphical element may be ordered based on referential data or by user input. In some embodiments, the simulation data from one circular graphical element is connected to simulation data from another circular graphical element. In these embodiments, the circular viewer radially aligns the connected simulation data. In each circular graphical element, the circular viewer may visually distinguish portions of the simulation data that are above a threshold differential from the baseline cell state. The circular viewer may receive inputs from a user of the simulation system to select portions of the simulation data in a circular graphical element. In response, the circular viewer may visually distinguish the selected portion of simulation data in the circular graphical element. Moreover, the circular viewer may visually distinguish other portions of simulation data from other circular graphical elements that may be correlated to the selected portion. In additional embodiments, the circular viewer displays additional identifiers. In one embodiment, the circular viewer displays input connectors and output connectors between circular graphical elements corresponding to correlative inputs and outputs of intermediary compounds or products between simulation data in different circular graphical elements.

The circular viewer provides ease in observing effects of the simulation in the simulation data. The circular viewer may visually distinguish interesting simulation data that is above a threshold differential from the baseline cell state. As the simulation data is grouped into different biological categories which are then separately displayed in the circular graphical elements, the visually distinguished simulation data over all the circular graphical elements provide an ease in visualizing correlative simulation data over the various biological categories. As one example, the circular viewer may provide an ease in observing an upregulation of protein production correlated with an upregulation of a gene expression. Moreover, in embodiments where the circular viewer may update to display simulation data over different time steps in the simulation, the circular viewer provides ease in comparing effects of the simulation over the simulation's run time. In one example, the circular viewer may display a long term effect of an upregulation of a specific gene as downregulation of a metabolic process. Upon viewing the circular viewer, the user may learn interesting correlations in the simulation data through observing which portions of the simulation data are visually distinguished by the circular viewer. The user may focus further experimentation, either in silico or in vivo/in vitro using wet lab, due to the newly observed portions of simulation data. In some instances, the user may follow up with adjusting simulation parameters to narrow the simulation for studying the newly learned correlations corresponding to visually distinguished simulation data.

As a result of the specific construction of the circular viewer and the information presented, a user may have an insight that leads to a new or further simulation being performed. Additionally, insight garnered from the circular viewer may allow for specification of an in vitro or in vivo experiment to be performed in a web lab (e.g., using cell cultures). This may be the case, for example, for target identification or compound (hit) evaluation for a drug discovery process. Additionally, the circular viewer may prevent unneeded simulations. Due to the multitude of data synthesized by the circular viewer, unneeded simulations may be avoided where the data was present in an already performed simulation, where the desired information was not identified by the user due to the unstructured and sprawling nature of the simulation data in the absence of the circular viewer. Reducing the number of in silico simulations and resulting number of datasets produced by the simulations may then correspond to a reduction of the parameter space of the web lab tests. Wet lab tests are costly in terms of employee time, physical resources required, physical space, and so on. Any reduction in the parameter space of wet lab evaluation would generate tangible benefits in this regard.

Other graphical elements may contain various menus or displays for performing other tasks with the simulation data. A simulation map may be generated which is a graphical element that presents reaction nodes of a linked network of pathways in the biological cell's processes, wherein each reaction node contains some number of reactions within the linked network. Some graphical elements may present informational panels providing details of various items, such as simulation data, reaction data, descriptions of reactants, descriptions of products, etc. Additionally the GUI may allow the user to select portions of the simulation data in the circular viewer or other graphical elements. Responsive to the user selection, the GUI may provide additional information through the other graphical elements via informational panels.

BRIEF DESCRIPTION OF THE DRAWINGS

FIG. 14A-D are illustrative examples of the outcome type bar, in accordance with an embodiment.

DETAILED DESCRIPTION

I. Simulation Model of a Simulation

Figure 1:
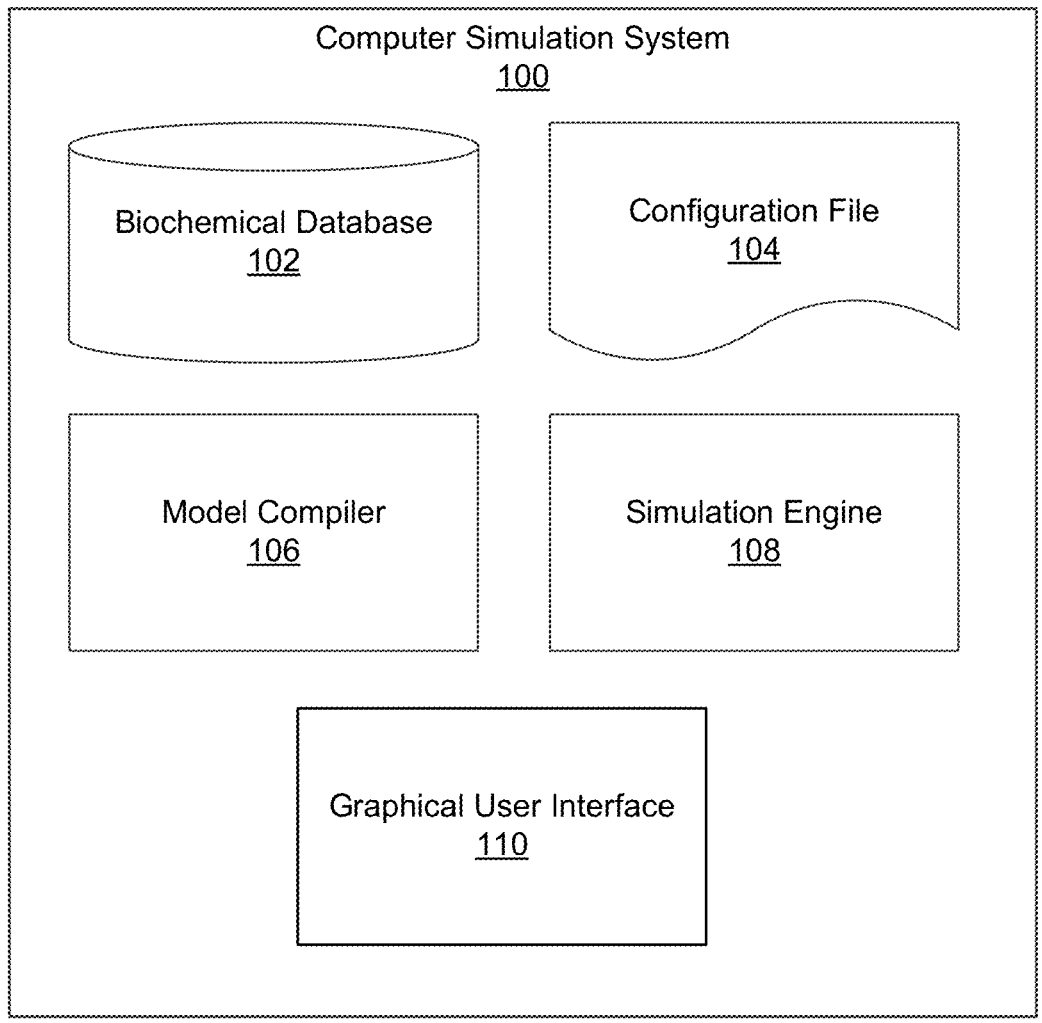
FIG. 1 is a block diagram illustrating computational components of a simulation system for modeling the behavior of a biological cell, in accordance with an embodiment.

FIG. 1 is a block diagram illustrating computational components of a computer simulation system 100 (herein referred to as simply "simulation system") for modeling the behavior of a biological cell, in accordance with an embodiment. Depending on the embodiment, each component of the simulation system 100 may be implemented on one or more servers or other computational devices that are configured to communicate over a network (e.g. the Internet, a local area network, etc.). Alternatively, all computational components may be locally present on a single computational device. The computational components making up the simulation system 100 shown in FIG. 1 are a biochemical database 102, a working data file 104, a model compiler 106, a simulation engine 108, and a GUI 110. The GUI 110 may be the GUI 1200, and is described in further detail with reference to FIG. 12.

The biochemical database 102 is a database that stores data regarding molecules and processes that may be present or may occur in a biochemical environment simulated using the simulation system 100. The biochemical database 102 stores compositional data for each molecule that may be of use in the simulation, as well as data specifying how each molecule may be involved in one or more processes simulated by the simulation system 100. The biochemical database 102 may, more specifically, include information describing an organism at various levels of specificity. For example, on a more detailed level, the biochemical database 102 includes a catalog of an organism's genes, transcripts, proteins, etc. At a higher level of generality, the biochemical database 102 may include structures such as an organism's protein complexes. Although any database structure may be used to implement the biochemical database 102, in one embodiment the biochemical database 102 is implemented as a bipartite reaction network, which is described in further detail with reference to FIG. 2. Those of skill in the art will recognize that the same biochemical could be stored in another type of data structure.

The working data file 104 (sometimes referred to as the working file) is a set of instructions for configuring the simulation system 100. The simulation system 100 may be configured to simulate a single set of molecules and processes and, therefore, is not configured separately for each use of simulation system 100. Alternately, the working file 104 is used to select the molecules and processes to be simulated in the simulation system 100, and is therefore configured separately for each use of the simulation system 100. Additionally, the working file 104 may designate the specific cell functions to be modelled as well as the models to be included in the simulation system 100. Furthermore, the working file 104 may include parameters for one or more submodels included in the simulation system 100, as well as a set of initial conditions for each of those models.

The model compiler 106 uses working file 104 to compile the simulation system 100 so that simulations can be run. The model compiler 106 accesses the data retrieved from the biochemical database 102 and the working file 104 to generate various components of each simulation, examples of which include but are not limited to: a stoichiometric matrix, a bipartite network link molecule and process nodes, initial flux vectors that describe the rate of production and/or consumption of molecules, and quantities prior to a model being run for the first iteration, an objective function for each model, and any constraints on any of the models. After processing the various components of the simulation, the model compiler 106 outputs a simulation configuration data file (sometimes referred to as a configuration file or sim-config file). The configuration file is an input to the simulation engine 108 to generate a simulation of the cellular process described by the working file 104. In some implementations, the configuration file is a set of instructions to be executed by the simulation engine to accurately generate a simulation.

The simulation engine 108 manages the execution of the configuration or simconfig file produced by the model compiler 106 to simulate a biochemical process using the simulation system 100. The simulation engine 108 may initialize a given simulation using the initial conditions as constructed by the compiler 106 and as contained in the simconfig file. The simulation engine 108 creates an initial state vector, which includes the concentration of each molecule included in the simulation. The simulation engine 108 creates any initial exchange flux values into and out of each model in the simulation, which sets an initial rate of consumption and production for the associated molecules. The simulation engine 108 then iterates through a time step of the simulation, running the models of the simulation with the input state vectors and fluxes. Generally, this involves the simulation engine 108 arriving at a solution of the model for a first time step after the initial state, where the time step is of a predetermined length. The solution for each model for that time step may include, but is not limited to, the concentrations of the molecules output by each model, the fluxes of those molecules, and any changes to the overall biochemical environment (e.g. temperature changes, pH changes, etc.) caused by the processes being simulated by each model.

After the completion of the initial time step of the simulation, the simulation engine 108 updates the initial state vectors, flux vectors, and any other relevant state vectors with the output of the initial time step. As a specific example, the simulation engine 108 may use the fluxes determined during the running of the models multiplied by the length of the predetermined time step to determine the new concentrations of the molecules included in the models of the simulation. As another specific example, the simulation engine 108 may also calculate the exchange fluxes that connect each model with each other model in the simulation. The simulation system 100 then runs a second time step of the simulation similarly to the first time step using the updated state vectors and any other parameters of the simulation. The simulation engine 108 continues this process for a number of time steps or until reaching a termination state or receiving a termination input.

II. Biochemical Database

Figure 2:
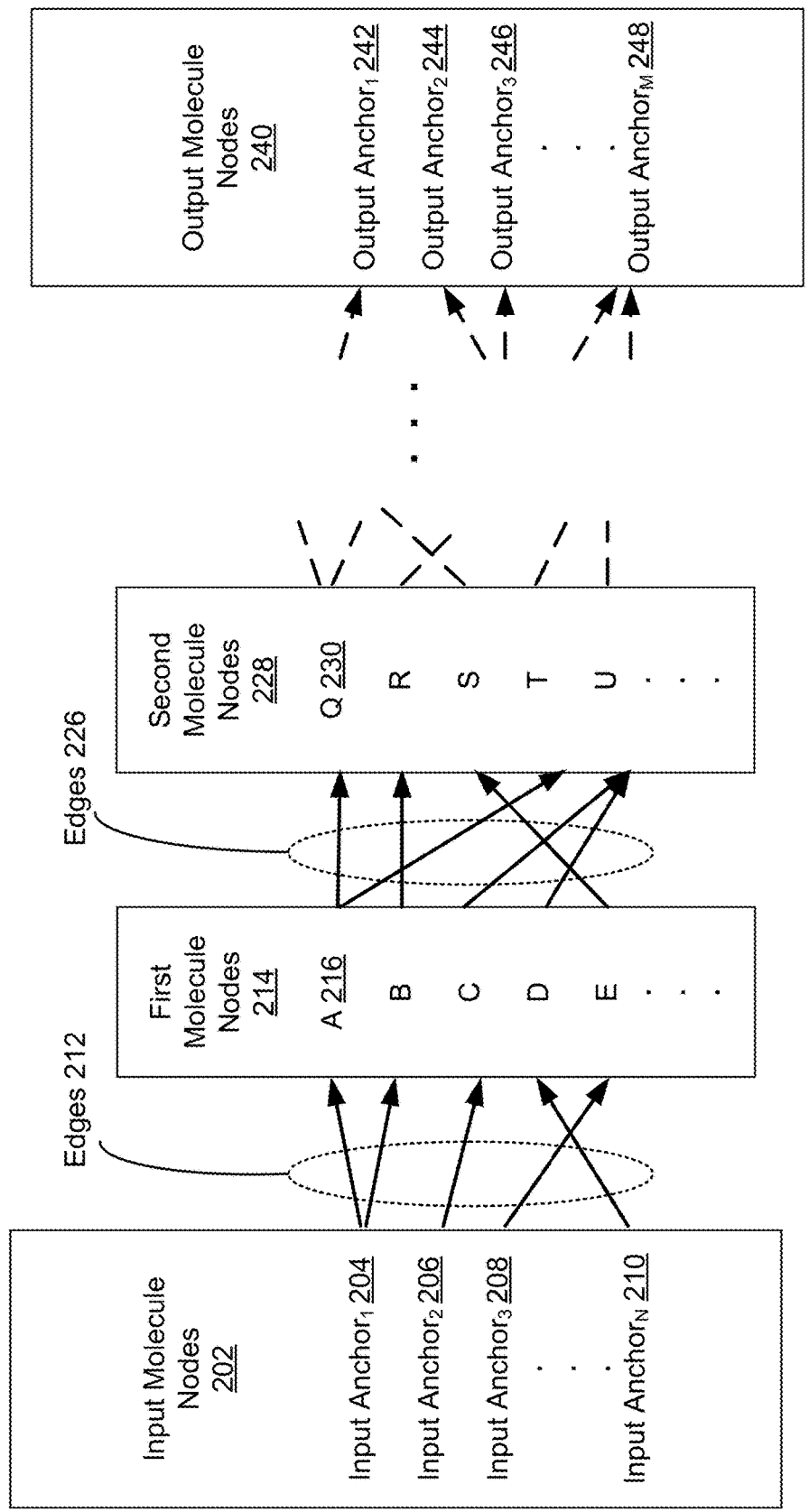
FIG. 2 is a block diagram illustrating a cell reaction network, structured in an exemplary embodiment as a bipartite graph.

FIG. 2 is a block diagram illustrating a cell reaction network, structured in an exemplary embodiment as a bipartite graph. The reaction network 200 includes input molecule nodes 202. The input molecule nodes 202 represent the input molecules of a given cell process (e.g., as implemented within the simulation system 100 by one of several sub-models, as discussed with respect to FIG. 3 below), and are the input boundary of the reaction network 200 of either the entire cell or some portion thereof if the network is created for a specific cell process. Each of the input molecule nodes 202 is connected to at least one process node to form a bipartite graph of connected molecule nodes and process nodes (not shown). In this structure, molecule nodes are connected by edges to the process nodes of the biochemical reactions they are involved in, which are in turn linked by edges to the molecule nodes they create, and so on. For simplification in FIG. 2, the process nodes and the edges linking process nodes to molecule nodes have been condensed and are shown and referred throughout as edges connecting molecule nodes. It is to be understood that the edges described herein are stored within a bipartite graph as process nodes with edges connecting each molecule node to its associated process nodes.

Thus as in the prior paragraph, in the example of FIG. 2 each of the input molecule nodes 202 is connected to at least one of the first molecule nodes 214 with edges 212. The first molecule nodes 214 represent the first products of. The first molecule nodes 214 may be connected to the second molecule nodes 228 with edges 226. Depending on the number of molecule nodes in the reaction network 200, there may be any number of additional molecule nodes and edges. Finally, the output molecule nodes 240 represent the outputs of a given model within the simulation, and are the output boundary of the reaction network 200.

II.A. Scope of the Bipartite Network

The reaction network 200 includes all molecules, reactions and reaction pathways that are used in a steady-state mathematical simulation of a cell. For example, the reaction network 200 contains all molecules, reactions and reaction pathways used in a metabolic model, a cell transcription model, a cell translation model, a cell wall generation model, etc.

II.B. Molecule Nodes

As described herein, within a cell reaction network structured as a bipartite graph, molecule nodes, such as molecule nodes 202, first molecule nodes 214, second molecule nodes 228, and output molecule nodes 240 are nodes of the bipartite graph that represent a molecule or chemical element that is present in a reaction within a cell. A molecule node may represent small molecules such as water, carbon dioxide, protons, etc. or macromolecules such as proteins, lipids, alcohols, organic acids, vitamins, etc. As stored in the reaction network 200, a molecule node may contain a plurality of metadata fields describing the molecule. The metadata of a molecule node may include the molecule name, a molecule formula, an amino acid sequence, a macromolecular structure, electrical charge, chemical or physical properties (pKa, melting point, solubility, etc.) and any component molecules. Additionally, some non-physical properties may be included in the metadata of a molecule node including drug interaction, 3D structure etc. A molecule node need not contain information for each one of the previously described metadata categories.

II.C. Input Nodes

Input molecule nodes 202 represent molecules that are inputs to cell reactions, and thus to the reaction network 200. The input molecule nodes 202 include molecules that are inputs to cell reactions from an upstream cellular process, as well as molecules in the cytoplasm of a cell, and molecules that the cell model is capable of sourcing from its external environment and using in a cell reaction network. All of the input molecule nodes 202 and input anchors have an input flux value solution. The input flux value solutions for the input molecule nodes 202 may be determined by solving one or more of the models of the simulation using the other molecules and reactions of the reaction network 200. The input flux value solution for a molecule node in the reaction network 200 represents the rate at which that molecule enters the cell reaction network at steady state. The input flux of a molecule node can be conceptualized as the "demand" for the molecule by the model. In some examples, the flux value solutions of all input anchors and input molecule nodes 202 are non-zero. In other examples, input flux value solutions for a subset of the input molecule nodes 202 and input anchors are 0.

Molecules that are input molecule nodes 202 are "anchored" within the reaction network 200 and stored within the input molecule nodes 202 as input $anchor_1$ 204, input $anchor_2$ 206, input $anchor_3$ 208 through input $anchor_N$ 210, where N is the total number of input molecule nodes 202. As used herein, "anchored" nodes (such as input anchor$_1$ 204, input anchor$_2$ 206, input anchor$_3$ 208 through input anchor$_N$ 210) are molecule nodes that are always included in FBA analysis of the reaction network 200. As described above the molecules represented by the input anchors input anchor$_1$ 204, input anchor$_2$ 206, input anchor$_3$ 208 through input anchor$_N$ 210 need not be present within the cell during mathematical simulations using the reaction network 200.

In an example, the input anchor$_1$ 204 represents a molecule that is a direct input to a particular reaction of the cell from an upstream cellular process. For example, the upstream cellular process may be transcription, such that the input anchor$_1$ 204 molecule is an RNA molecule previously used in the cell and that is then broken down in the cell. The input anchor$_1$ 204 has an input flux value solution, as calculated from a mathematical model of the reaction network 200, such as an FBA model for metabolism. Input anchor$_1$ 204 is thus at the "boundary" to the reaction network 200, and enters the reaction network 200 at a rate given by its input flux value solution, representing the rate of consumption of RNA.

In another example, the input anchor$_2$ 206 is also a direct input to a reaction within the cell, however it is not present within an upstream cellular process and is instead sourced by the cell through a membrane transport pathway, or some other cellular mechanism. The input anchor$_2$ 206 may not have a concentration within the cell during mathematical simulation of the reaction network 200. Alternatively, the input anchor$_2$ 206 may be present in the environment outside of the cell, and through a membrane transport pathway, the cell delivers the input anchor$_2$ 206 to the reaction network 200. The input anchor$_2$ 206 may contain metadata linking it to the membrane transport pathway, or other cellular mechanism from which it is sourced to the reaction network 200.

In another example, the input anchor$_3$ 208 may have a constant or near-constant presence within the cytoplasm of the cell, such that the molecule of the input anchor$_3$ 208 is stored at some concentration external to the cell reaction network, but within the cell model. The input flux of the input anchor$_3$ 208 thus represents a movement of the input anchor$_3$ 208 from the cell's storage concentration to the reaction network 200.

II.D. Process Nodes Shown as Edges

The process nodes and edges linking molecule nodes to process nodes in a bipartite graph are shown and referred to throughout as edges for simplification. As referred to throughout, each edge is a process node in the bipartite graph with connecting edges to its associated molecule nodes. Edges 212 connect input molecule nodes 202 to first molecule nodes 214. Specifically, a single edge 212 connects a single input molecule node 202 to a single molecule node in the first molecule nodes 214. Each edge in the edges 212 represents a chemical reaction or process converting the input molecule to a molecule in the first molecule nodes 214. For example, as shown in the reaction network 200, the input anchor$_1$ 204 is connected by an edge in the edges 212 to molecule A 216 in the first molecule nodes 214. This edge represents a chemical reaction or process in which the input anchor$_1$ 204 is a reactant, and molecule A 216 is a product.

The direction of the edges 212 (e.g., pointing from input molecule nodes 202 to first molecule nodes 214) indicates the direction of the chemical reaction. Thus an edge pointing from a first molecule to a second molecule indicates that the first molecule is a product and the second molecule is a reactant in the chemical reaction. As described herein, an edge "leading out" of a molecule node indicates that the chemical reaction uses that molecule as a reactant, and that the direction of the chemical reaction in the cell reaction network is forward, away from that molecule. As described herein, an edge "leading into" a molecule node indicates that a chemical reaction produces that molecule as a product, and that the direction of the chemical reaction in the cell reaction network is forward toward that molecule. For example, edges 212 lead out of the input molecule nodes 202 and lead into the first molecule nodes 212. Specifically, an edge in the edges 212 leads out of input anchor$_1$ 204 and into molecule A 216 of the first molecule nodes 214.

The reaction network 200 then includes second molecule nodes 228, which are shown connected to first molecule nodes 214 with edges 226. The first molecule nodes 214 may be reactants in chemical reactions that produce second molecule nodes 228 as products. The edges 226 indicate which of the first molecule nodes 214 are converted to second molecule nodes 228, as well as the direction of the chemical reactions. Not all of the first molecule nodes 214 may be converted to second molecule nodes 228. This may be due to some of the first molecule nodes 214 and/or second molecule nodes 228 being unused or unmade molecule nodes. In some examples, some of the second molecule nodes 228 may be reactants in chemical reactions that produce the first molecule nodes 214 as products, such that the edges 226 lead out of these second molecule nodes 228 and into the first molecule nodes 214. This may be due to cyclical portions of the reaction network 200.

Edges 212 and 226 may store metadata further specifying the details of the chemical reactions within the reaction network 200. For example, edges 212 and 226 include the stoichiometric balance between the two molecules they are connected to. The edge connecting molecule A 216 and molecule Q 230 includes the stoichiometry of the reaction converting molecule A 216 to molecule Q 230. The edges 212 and 226 may also include the enzymes, cofactors, or other facilitating molecules involved in a chemical reaction. Edges 212 and 226 may include protein folding operations and the movement of these facilitating molecules in the cell, as well as rates and locations and numbers of active sites. Additionally or alternatively, edges 212 and 226 store activation energy, Gibbs free energy change, kinematic properties and other thermodynamic properties known in the art describing the chemical reaction. Edges 212 and 226 may store this and any additional information relevant for describing the chemical reactions or processes that convert molecule nodes from reactants to products within the reaction network 200.

Edges 212 and 226 have associated flux values, which are rates at which molecule nodes are converted from reactants into products, however, since these edges are not at the boundaries of metabolism, they may not be solved for in an FBA model using the reaction network 200. The direction of flux through the reaction network 200 and between molecule nodes in indicated by the direction of the edge. For example, the edge leading out of molecule A 216 and into molecule Q 230 has an associated flux rate, which indicates the rate at which molecule A 216 is converted into molecule Q 230. The flux values of the input anchors are the input flux values of the reaction network 200, and may be determined through a mathematical simulation of the reaction network 200, such as an FBA model simulation.

II.E. Output Nodes

There may be any number of molecule nodes within the reaction network 200. Ultimately, the reaction network 200 ends with the output molecule nodes 240. Output molecule nodes include any number of output anchor molecules, such as output anchor$_1$ 242, output anchor$_2$ 244, output anchor$_3$ 246 through output anchor$_M$ 248, where M is the total number of output molecules of the reaction network 200. Each of the output molecule nodes 240 represent the outputs of metabolism as shown as the reaction network 200. The output molecule nodes 240 may thus be used in cellular processes downstream from metabolism, stored within the cell, output through a membrane transport pathway, and/or any other use in the cell external to metabolism. Each of these cellular processes may have their own associated mathematical model and simulation.

All of the output molecule nodes 240 and output anchors have an output flux value solution. The output flux value solutions for the output molecule nodes 240 may be determined by solving an FBA model using the reaction network 200. The output flux value solution for a molecule node in the reaction network 200 represents the rate at which that molecule leaves the network at steady state. The output flux of a molecule node can be conceptualized as the metabolic "production" of the molecule. In some examples, the flux value solutions of all output anchors and output molecule nodes 240 are non-zero. In other examples, output flux value solutions for a subset of the output molecule nodes 240 and output anchors are 0.

Each of the output molecule nodes 240 are designated as "anchored" nodes. Thus output anchor$_1$ 242, output anchor$_2$ 244, output anchor$_3$ 246 through output anchor$_M$ 248 are isolated from the rest of a reaction network 200 when the reaction network 200 is simplified and condensed. Not all of the output anchors need be produced during a given simulation of the reaction network 200, however at least one reaction pathway within the reaction network 200 must be capable of producing the output molecule nodes 240 as its final product. Thus at least one edge in the bipartite network leads into each of the output molecule nodes 240.

Input molecule nodes 202, first molecule nodes 214, second molecule nodes 128, and output molecule nodes 240 may each be stored as arrays, or in any other data structure known in the art. Input molecule nodes 202, first molecule nodes 214, second molecule nodes 128, and output molecule nodes 240 may be different dimensional arrays, and thus need not have the same number of components. Input molecule nodes 202, edges 212, first molecule nodes 214, edges 226, second molecule nodes 128, and output molecule nodes 240 are populated into the reaction network 200 as molecule nodes connected to process nodes from a variety of sources, such as primary literature, databases, biochemistry textbooks, conference presentations, or any other primary source literature. As initially input into the reaction network 200, there may be redundancies in the reaction network 200, or reaction pathways between molecule nodes that are dead-ends, such that at steady state of the reaction network 200, there is zero flux through the pathway.

The biochemical relation between all molecules within a reaction network is thus converted to a structure of reaction edges (e.g., process nodes) and connected molecule nodes to form the reaction network 200. To identify features of the reaction network, such as the relative importance of reaction pathways, or dead-end pathways, one can analyze the structure of the reaction network 200. Specifically, the biochemical relation of each molecule and its corresponding molecule node to other molecules and molecule nodes is given by the edges into and out of each node. By categorizing molecule nodes according to the number of edges into and out of each node, the reaction network 200 can be condensed and simplified, and important reaction pathways identified.

III. Sub-Models in Cell Modeling

Figure 3:
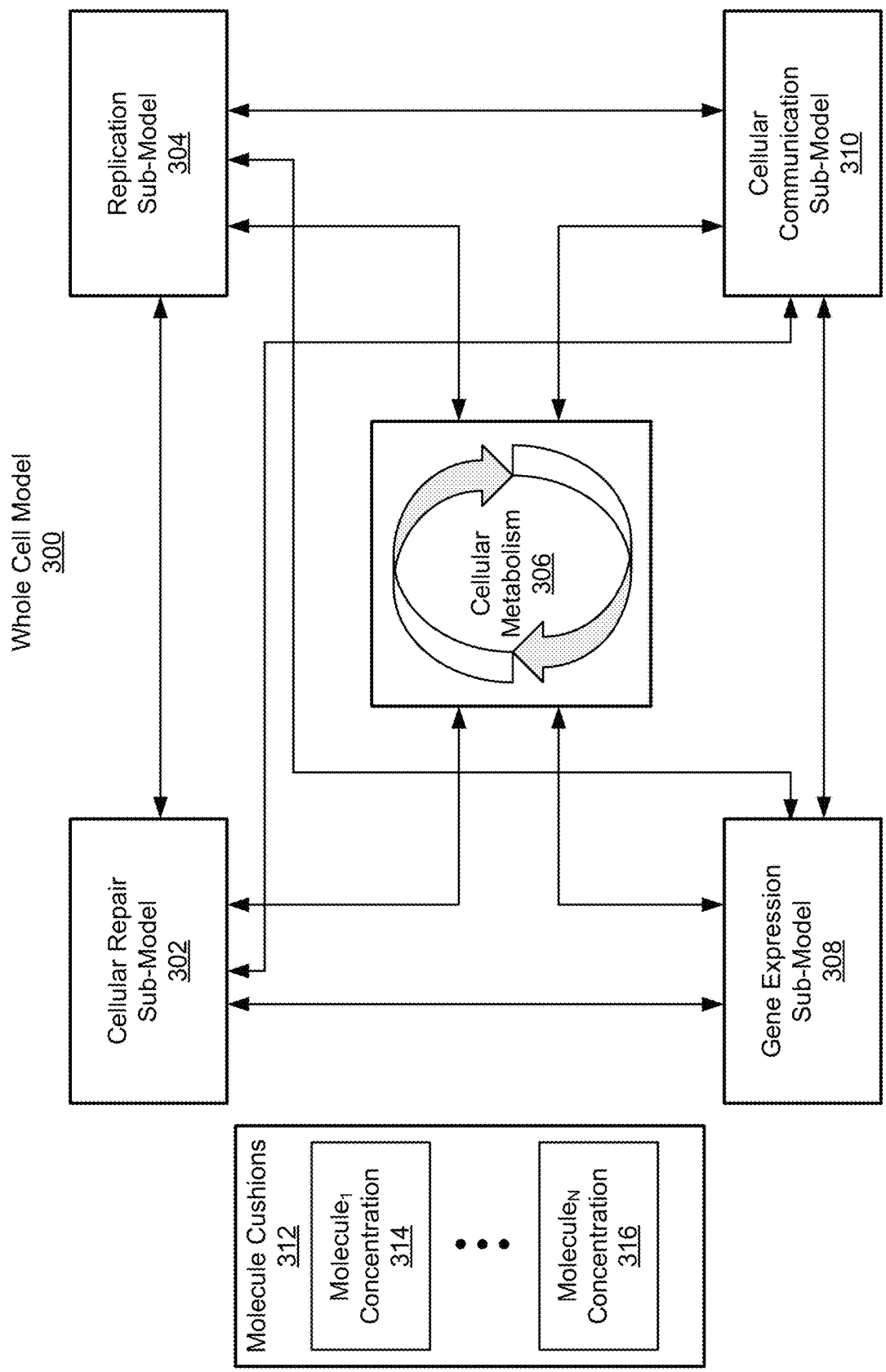
FIG. 3 is a block diagram of a full cell model, according to one embodiment.

FIG. 3 is a block diagram of a full cell model 300, according to one embodiment. The full cell model 300 contains a cellular metabolism 306 with any number of sub-models which input and/or output with other sub-models or the cellular metabolism 306. The sub-models include the cellular repair sub-model 302, the replication sub-model 304, the gene expression sub-model 308, and/or the cellular communication sub-model 310. The arrows leading to the cellular metabolism 306 represent the input flux and/or output flux values between the cellular metabolism 306. Arrows between sub-models and cellular metabolism 306 may also represent the supply of molecules from these sub-models to cellular metabolism 306.

As shown in FIG. 3, arrows lead from sub-models into cellular metabolism 306 and from cellular metabolism 306 into sub-models. This is an illustration of the fact that many cellular processes contain molecules and reaction pathways that are both inputs into cellular metabolism 306 and which are produced by cellular metabolism 306. Thus the sub-models shown in FIG. 3 may be both upstream sub-models and downstream sub-models, as described with reference to FIG. 1. The interactions between sub-models and cellular metabolism 306 may be coordinated by a single dataset that aggregates changes within the full cell model 300, such that each of the sub-models and cellular metabolism 306 receive and transmit information to the single dataset, rather than to each other.

In addition to molecule concentrations within sub-models and cellular metabolism 306, the full cell model 300 may include molecule cushions 312 that exist outside of system of supply and demand between the sub-models and cellular metabolism 306. The molecule cushions 312 represent reserves of molecules within the cellular environment. For example, molecule cushions 312 may be molecules that exist within a cell's cytoplasm, and which are available to molecular processes when needed. Molecule cushions 312 contain different reserve concentrations of different molecules. For example, a first molecule, molecule$_1$, may have a concentration molecule$_1$ concentration 314. If molecule$_1$ is a molecule that has a large flux value or demand within the system of sub-models and cellular metabolism 306, then the reserve concentration of molecule$_1$ may be larger than other molecules with smaller demand. Thus the concentration of molecules within molecule cushions 312 may be proportional to the flux value associated with the molecule in cellular metabolism, the aggregate demand for the molecule within the sub-models, and/or any other measurement of demand within the system of sub-models and cellular metabolism 306. The molecule cushions 312 ensure that sudden increases in demand for a molecule within the full cell model 300 do not result in complete depletions of a molecule within the full cell model 300.

There may be any number of molecules within molecule cushions 312. A total of N molecules, represented by molecule$_N$ concentration 314, are assigned reserve concentrations within molecule cushions 312. In some examples, all molecules within the full cell model 300 are assigned reserve concentrations within molecule cushions 312. In other examples, molecules with demand and/or flux values above a threshold are assigned reserve concentrations within molecule cushions 312, such that a subset of the molecules within the full cell model 300 representing the primary flow of molecules are stored in molecule concentrations molecule$_1$ concentration 314 through molecule$_N$ concentration 314.

The effect of the molecule cushions 312 on the full cell model 300 is that the molecule cushion concentrations allow the demand for a molecule to instantaneously (e.g., for a given single time step evaluating the subunits) exceed supply without disrupting the full cell model 300. This allows the production network to continue to function as a demand load is applied to the system of the full cell model 300, giving the cell time to increase production of the molecule to meet the new demand.

IV. Circular Viewer in a Graphical User Interface of the Simulation System

Figure 4:
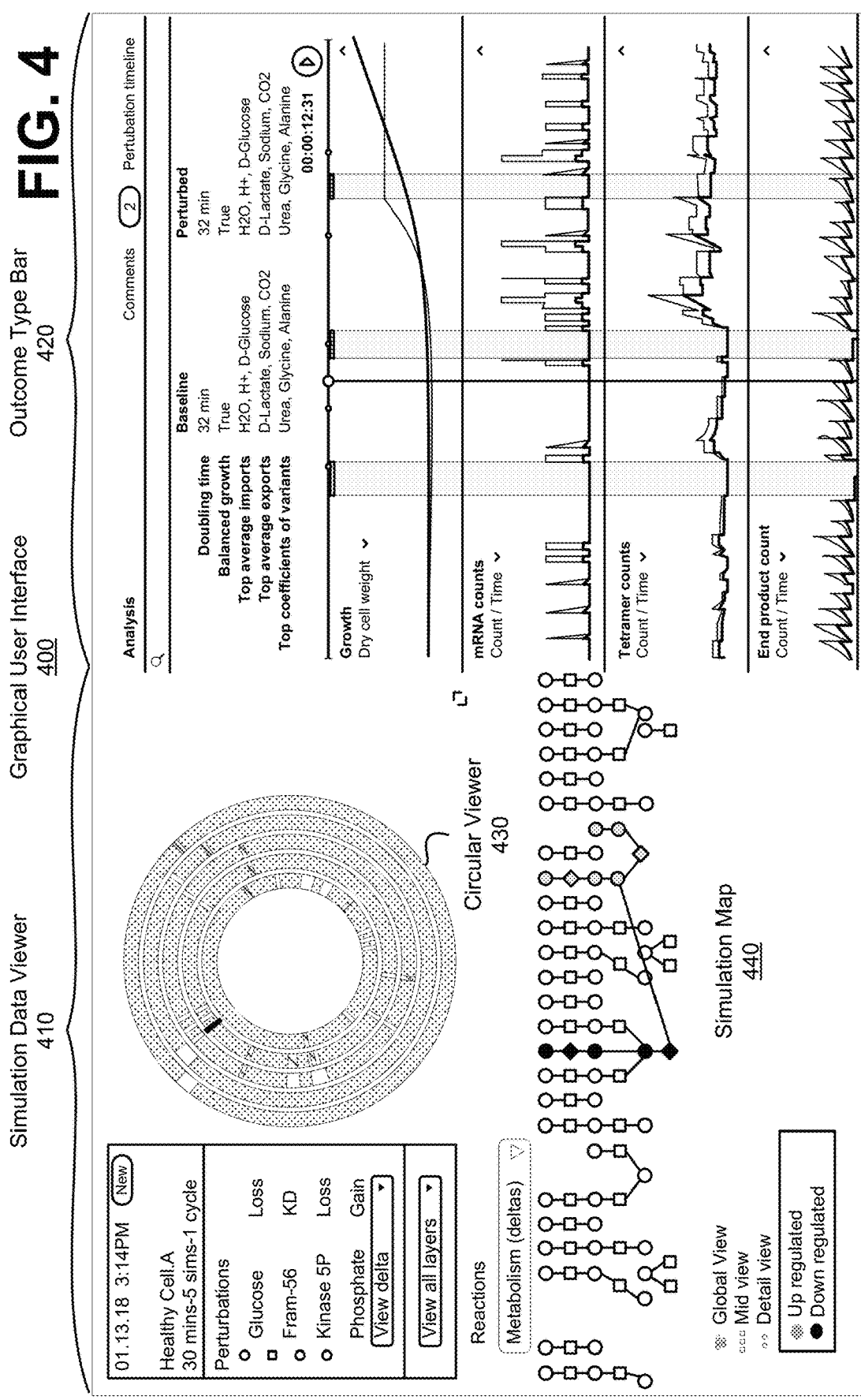
FIG. 4 is an illustration of a graphical user interface (GUI) of the simulation system, in accordance with an embodiment.

FIG. 4 is an illustration of a graphical user interface (GUI) 400 of the simulation system, in accordance with an embodiment. The simulation system 100 runs one or more simulations generating a separate set of simulation data per simulation. Collectively, a set of simulations is herein referred to as an "experiment" for convenience. The simulation system presents the simulation data for a simulation in the GUI 400 of the simulation system. The GUI 400 may be displayed through a display device of a computing device, specifically through a web page, an application, or another software or firmware mechanism. The GUI 400 presents a number of graphical elements within the GUI in different portions of a display area of the display device. Each such graphical element presents various pieces of information about the simulation and correspondingly the simulation data from one or more of the simulations. In one embodiment, the graphical elements of the GUI 400 include a simulation data viewer 410 and an outcome type bar 420, each of which is in a window of the GUI 400. The outcome type bar 420 will be described further in Sections V.B. in conjunction with FIGS. 13A-13C.

The simulation data viewer 410 includes a circular viewer 430 and a simulation map 440, according to an embodiment. The simulation map 440 is a graphical element which visually displays molecules and/or reaction nodes of the simulation with at least some of their associated connections. In the example embodiment of FIG. 4, the simulation map 440 occupies only a portion of the screen area allocated to the simulation data viewer 410.

The circular viewer 430 is another graphical element which displays simulation data in a plurality of concentric rings. Each of the concentric rings may correspond to simulation data corresponding to one of many macro-biological concepts, e.g., simulation data corresponding to DNA replication, to RNA transcription, to amino acid production, to peptide production, to protein production, to cell wall generation, to cell transport of products, to cell metabolism, etc. The circular viewer 430 may visually distinguish portions of the simulation data that may be of interest to a user of the simulation system 100. One example of interesting simulation data to display includes simulation data that changes at least a threshold amount between time steps compared to the baseline cell state. Another example of interesting simulation data is a threshold up or down rate (up regulation or down regulation, respectively) for one of the quantities tracked by the model. In response to viewing the circular viewer 430 visually distinguishing portions of the simulation data, the user may learn new correlations between the different macro-biological concepts. With this knowledge, the user may focus the simulations to further study and explore the correlations displayed by the circular viewer 430.

The circular viewer 430 is also configured to respond to inputs received from the user via an input device (not shown). In one embodiment, the circular viewer 430 may be hidden or shown in response to a received input selection of a button. In another embodiment, the circular viewer 430 may visually distinguish one or more portions of simulation data in the rings corresponding to a user input. In another embodiment, the circular viewer 430 occupies a fixed portion of the simulation data viewer 410 similar to the simulation map 440. Alternately the circular viewer 430 may be of variable size or moved in response to user input.

Figure 5:
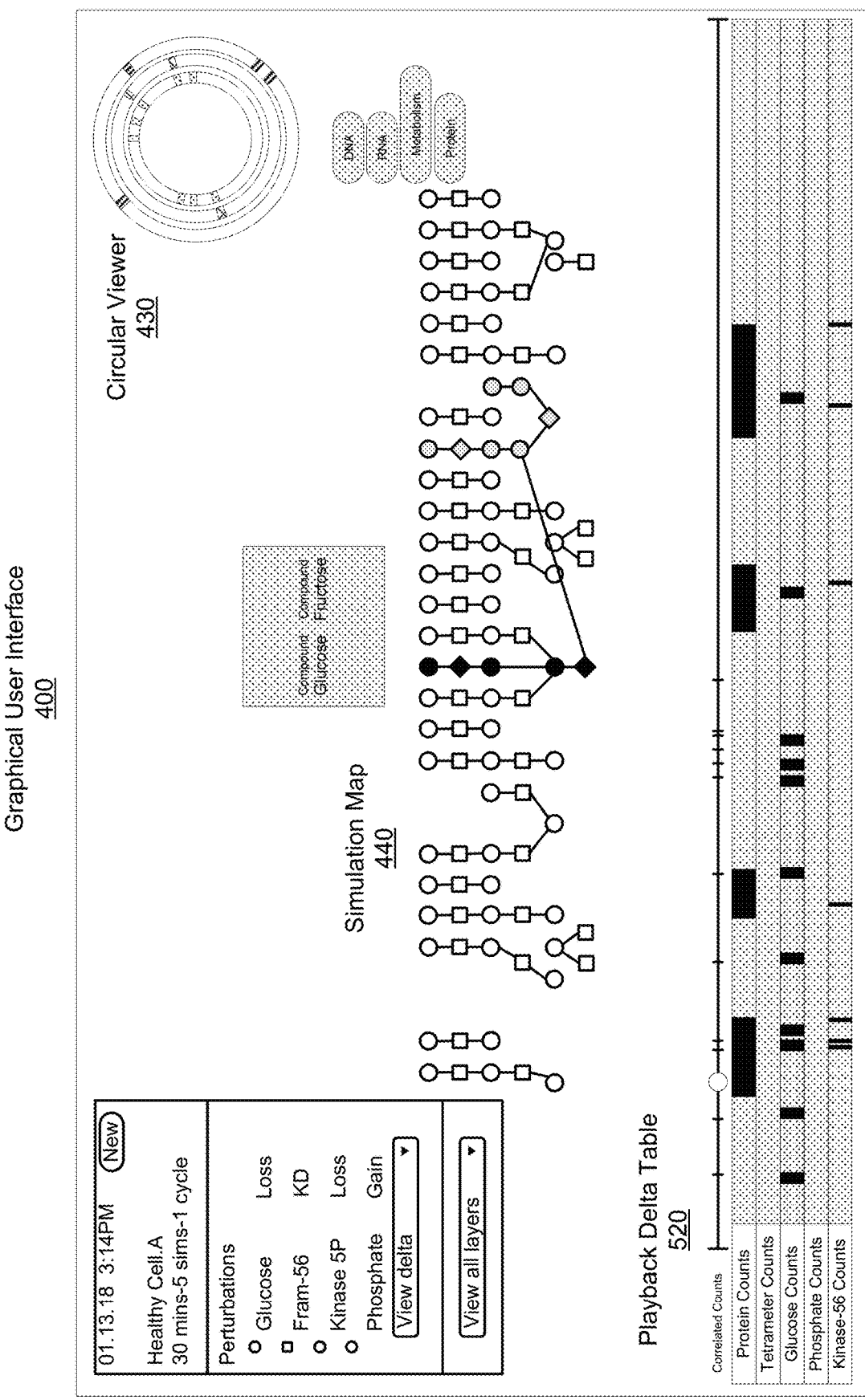
FIG. 5 is an illustration of an alternate embodiment of the GUI of FIG. 4.

FIG. 5 is an alternate embodiment of the GUI 400; the GUI 400 only currently displays the simulation data viewer 410. The simulation data viewer 410 contains the simulation map 440, the circular viewer 430, and a playback delta table 520. The playback delta table 520 differentially displays counts of simulation data (e.g., up regulation or up rates, down regulation or down rates, reactants, products, intermediary molecules, gene expression, reaction rates, etc.) that are above a threshold differential from the baseline cell state. In this example, the display shows these counts using different colorations, however other types of visual demarcations can be used. In one embodiment, the simulation's run time corresponds to one axis while various simulation data at each of a number of time steps of the simulation are placed on a perpendicular axis. In this embodiment, the playback delta table 520 visually distinguishes portions of the simulation data above a threshold differential at different time steps from the baseline cell state by highlighting the portions. The playback delta table 520 may also provide a button for receiving user input to walk through the simulation sequentially from one time step to another. Further, as playback proceeds, the simulation data displayed by the circular viewer 430 may be updated to display simulation data from the different time steps of the simulation.

Figure 6:
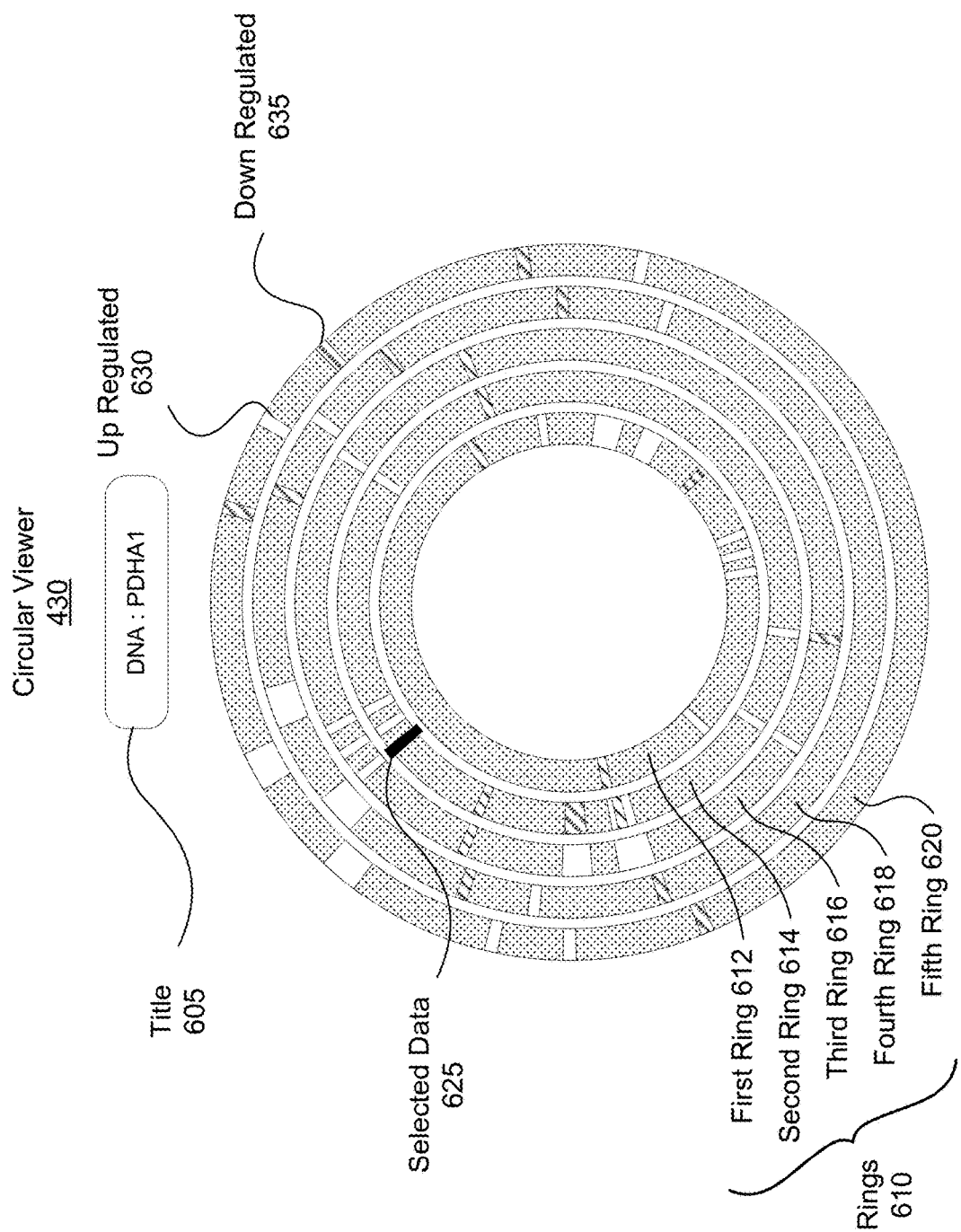
FIG. 6 is an illustration of a circular viewer, in accordance with an embodiment.

FIG. 6 is an illustration of the circular viewer 430 of FIG. 4, in accordance with an embodiment. The circular viewer 430 may contain a title 605 describing the simulation data being shown by the circular viewer. For example, the title 605 may display text corresponding to a name for the simulation or the title 605 may describe a time step of the simulation corresponding to the simulation data being shown in the circular viewer 430. The circular viewer 430 includes multiple concentric rings 610. Each of the concentric rings 610 is a circular graphical element that is shaped like an annulus with an outer radius and an inner radius, wherein a difference between the outer radius and inner radius is a width of the ring. To distinguish the rings 610 from a background of the GUI 400, the rings 610 may have any one or more of the following example visual demarcations: outlining, coloration, saturation, hue, shading, fill pattern, opacity, and other similar demarcations. The rings visually illustrate the simulation data in a non-textual form. Each ring visually illustrates simulation data corresponding to one of the biological categories, e.g., simulation data related to DNA replication, to RNA transcription, to protein translation, to metabolism, to cell transport of products, etc. In one embodiment, a first ring 612 corresponds to simulation data related to DNA replication; a second ring 614 corresponds to simulation data related to RNA transcription; a third ring 616 corresponds to simulation data related to protein translation; a fourth ring 618 corresponds to simulation data related to cell metabolism; and a fifth ring 620 corresponds to simulation data related to cell transport of products.

Simulation data may be ordered around a ring based on an established ordering of that simulation data, e.g., bacterial DNA is ordered in a circular fashion according to genomic ordering, or by user input ordering the simulation data. Simulation data from one ring may be aligned radially with simulation data from another ring if the simulation data of two rings are related. For example, if the first ring 612 is configured to display simulation data related to gene expression of a gene encoded in the DNA and the second ring 614 is configured to display simulation data related to the RNA transcription of the gene encoded in the DNA, the simulation data of the first ring 612 may be radially aligned with the simulation data of the second ring 614 so that the relevant data for these two rings appears at the same or substantially the same angular position on each ring.

After a simulation has been completed, the circular viewer 430 may visually distinguish portions of the simulation data that may be of interest in the rings 610. The portions of simulation data of interest may include portions of simulation data that are above or below a threshold differential from the baseline cell state. The simulation data that is above the threshold differential may be visually marked as up-regulated 630 simulation data; and the simulation data that is below the threshold differential may be differently visually marked as down-regulated 635 simulation data. In the example embodiment of FIG. 6, the circular viewer 430 visually distinguishes the up-regulated 630 simulation data with a solid fill pattern and the down-regulated 635 simulation data with a lined fill pattern. In the same or a different embodiment, the circular viewer 430 may use a color gradient, geometric scaling, or both to distinguish varying amounts of differential of the simulation data from the baseline cell state. In one some instances, the user may subsequently adjust simulation parameters to observe varying effects on the portions of simulation data that are above or below the threshold differential from the baseline cell state. In other instances, the user may select portions of simulation data that are visually distinguished to which the circular viewer 430 may respond (discussed in detail below).

When the simulation data is radially aligned from one ring to another, the visual distinction of the up-regulated 630 simulation data and the down-regulated 635 simulation data provides an ease to quickly identifying portions of the simulation data that are correlative from various biological categories. For example, along a radial portion of the circular viewer 430 the simulation data from all the rings 610 are up-regulated 630 which may hint to a correlative if not causative effect over various stages of the simulation. The user may further explore the correlative or causative effects to determine how those relationships may affect the cell model. For example, a down-regulation of DNA translation of a gene is correlated to a down-regulation of RNA transcription of the gene which is then correlated to an up-regulation of protein production of a protein linked to the gene.

Additionally, the circular viewer 430 may visually distinguish portions of simulation data corresponding to a user input. In one embodiment, the user selects some portion of the simulation data in the circular viewer 430. In some embodiments, the user selects a portion of the simulation data in the circular viewer 430 that has been visually distinguished due to the portion of simulation data being above the threshold differential. In either case, the circular viewer 430 responds by visually differentiating the selected data 625. In one embodiment, the circular viewer 430 may increase a size of the selected data 625. In the example embodiment of FIG. 6, the circular viewer 430 adjusts the selected data 625 to have a solid black fill pattern. In addition, the circular viewer 430 may display additional information corresponding to the selected data 625 on a separate portion of the simulation data viewer 410 or as an overlay atop the circular viewer 430.

Figure 7:
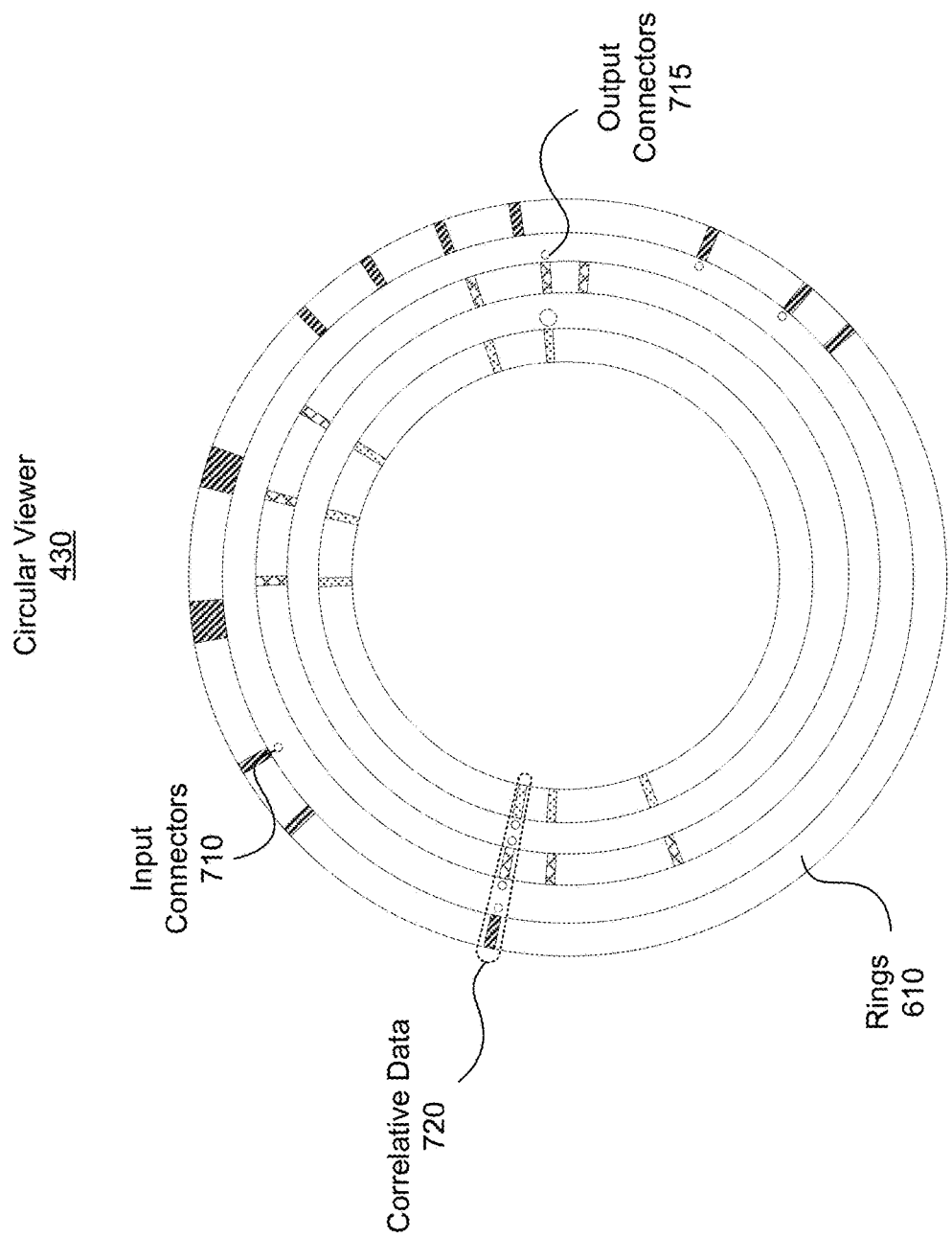
FIG. 7 is an illustration of a circular viewer with connectors, in accordance with an embodiment.

FIG. 7 is an illustration of the circular viewer 430 of FIG. 4 with connectors, in accordance with an embodiment. In the example embodiment of FIG. 7, the circular viewer 430 includes three rings 610, with various portions of simulation data from each ring highlighted. The circular viewer 430 may display connectors to visually link portions of simulation data from different rings 610. In one embodiment, the circular viewer 430 displays input connectors 710 and output connectors 715. The input connectors 710 and the output connectors 715 can link a portion of simulation data from one ring to another.

The input connectors 710 are symbol identifiers that are placed close to an interior of a ring 610 towards the center of the rings. Input connectors may be used in a variety of ways, and generally may be used to visually indicate any item of simulation data or derivation thereof. Often this data will be data different from that shown in the rings themselves. In one embodiment, the input connectors 710 indicate input compounds from different rings. For example, an input connector shaded one color may refer specifically to input compounds from a first ring while an input connector shaded another color may refer specifically to input compounds from a second ring. In another embodiment, input connectors 710 may also vary in another visual factor to indicate some degree of input from the other rings. For example, one input connector 710 of a larger size may represent greater input that another input connector 710 of a smaller size.

The output connectors 715 are symbol identifiers that are placed close to an exterior of a ring 610 towards the distal edge of the rings away from the center. Similarly to input connectors, output connectors may be used in a variety of ways, generally may be used to visually indicate any item of simulation data or derivation thereof, and are often used to visually indicate data not shown in the rings themselves or the input connectors. In one embodiment, the output connectors 715 refer to output of compounds from one ring to another. In one embodiment, a subset of simulation data from one or more rings 610 are highlighted and are radially aligned and connected with one or more input connectors 710 and output connectors 715. This subset of simulation data may be considered correlative data 720. The circular viewer 430 may visually distinguish the correlative data 720, e.g., by drawing an outline around the portions of simulation data that are highlighted but also radially aligned. The correlative data 720 may be determined by the circular viewer 430 as highlighted simulation data radially aligned across a threshold number of rings 610.

Figure 8:
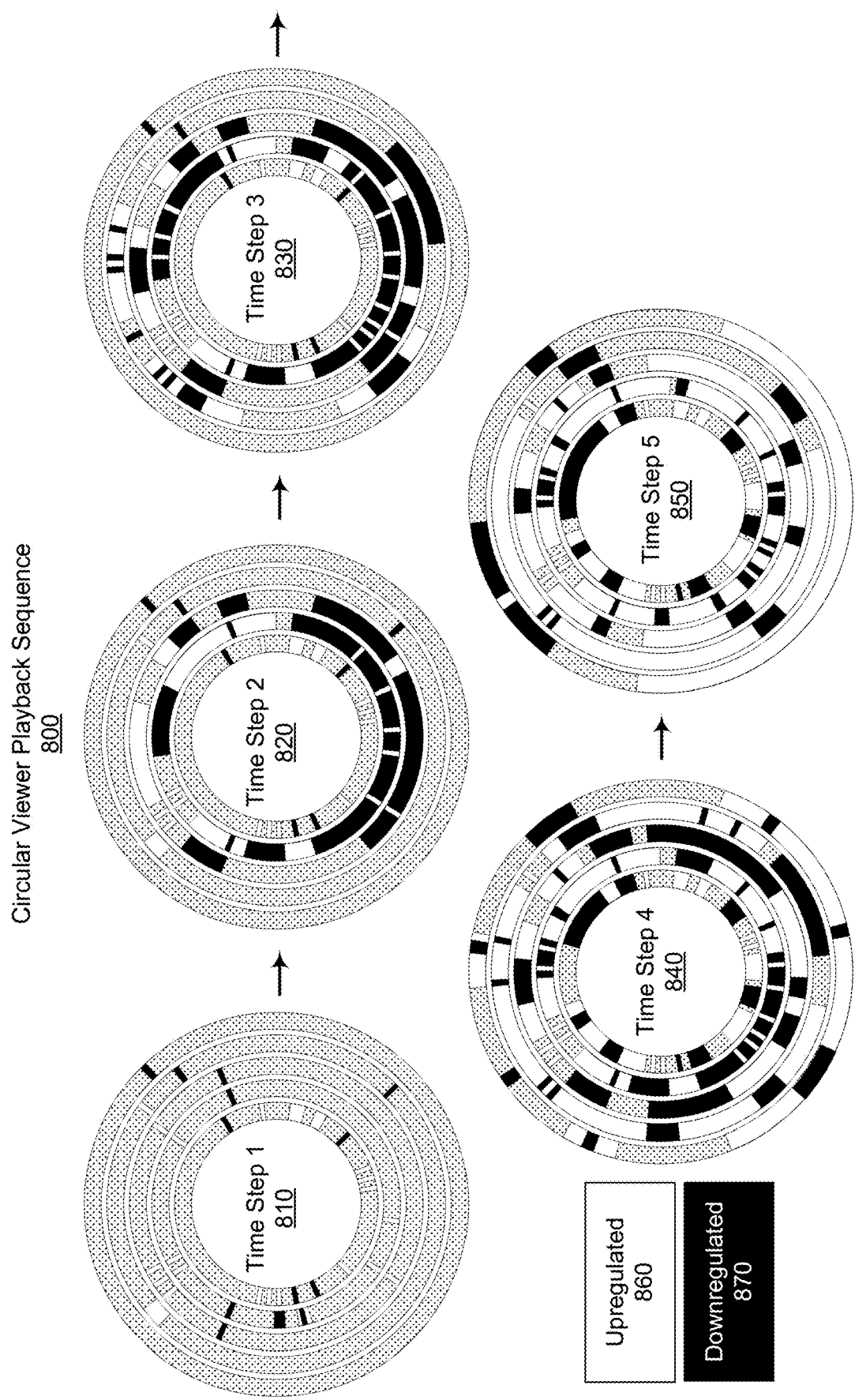
FIG. 8 is an illustration of the circular viewer 430 in multiple time steps in a playback sequence 800, in accordance with an embodiment.

FIG. 8 is an illustration of the circular viewer 430 in multiple time steps in a playback sequence 800, in accordance with an embodiment. In one embodiment, the simulation data viewer 410 includes a playback button to display simulation data of the simulation through all time steps of the simulation run time in the circular viewer 430. As the circular viewer 430 iteratively updates its displayed contents through the time steps sequentially, the circular viewer 430 may update the highlighted simulation data of interest at each time step. In one embodiment, the circular viewer 430 displays each time step and the corresponding simulation data over a time interval before updating to display a subsequent time step and the corresponding simulation data. In the illustration example of FIG. 8, the circular viewer 430 subsequently displays five time steps during the playback sequence 800: time step 1 810, time step 2 820, time step 3 830, time step 4 840, and time step 5 850. In this illustration, the circular viewer 430 highlights upregulated 860 and downregulated data 870 with a solid white fill pattern and a solid black fill pattern, respectively. In the time step 1 810, there are a few small portions of simulation data from the rings that are either upregulated 860 or downregulated 870. In the time step 2 820, there are a few large portions of simulation data that are either upregulated 860 or downregulated 870 within the second and third rings from the center of the circular viewer 430. This could be perhaps due to an increased effect from upregulation 860 and downregulation 870 in the first ring from the center. From time step 3 830 to the time step 4 840 to the time step 5 850, the circular viewer 430 displays greater portions of simulation data as either upregulated 860 or downregulated 870. The playback sequence 800 of a simulation provides a visual representation of the simulation's cell state progressively through the simulation. As the circular viewer 430 updates from one time step to the next, an ability to quickly compare adjacent time steps is effectively provided to the user of the circular viewer 430. The user may then further explore results of the simulation corresponding to various stages of the simulation.

Any combination of the functions described in FIGS. 6-8 can be implemented as part of the circular viewer 430, which may be a component of the GUI 400. Similarly, any combination of the principles described in FIGS. 6-8 can be used for identifying various portions of simulation data from multiple simulations simultaneously.

V. Scalable Multi-Viewer in a Graphical User Interface of the Simulation System

Figure 9A:
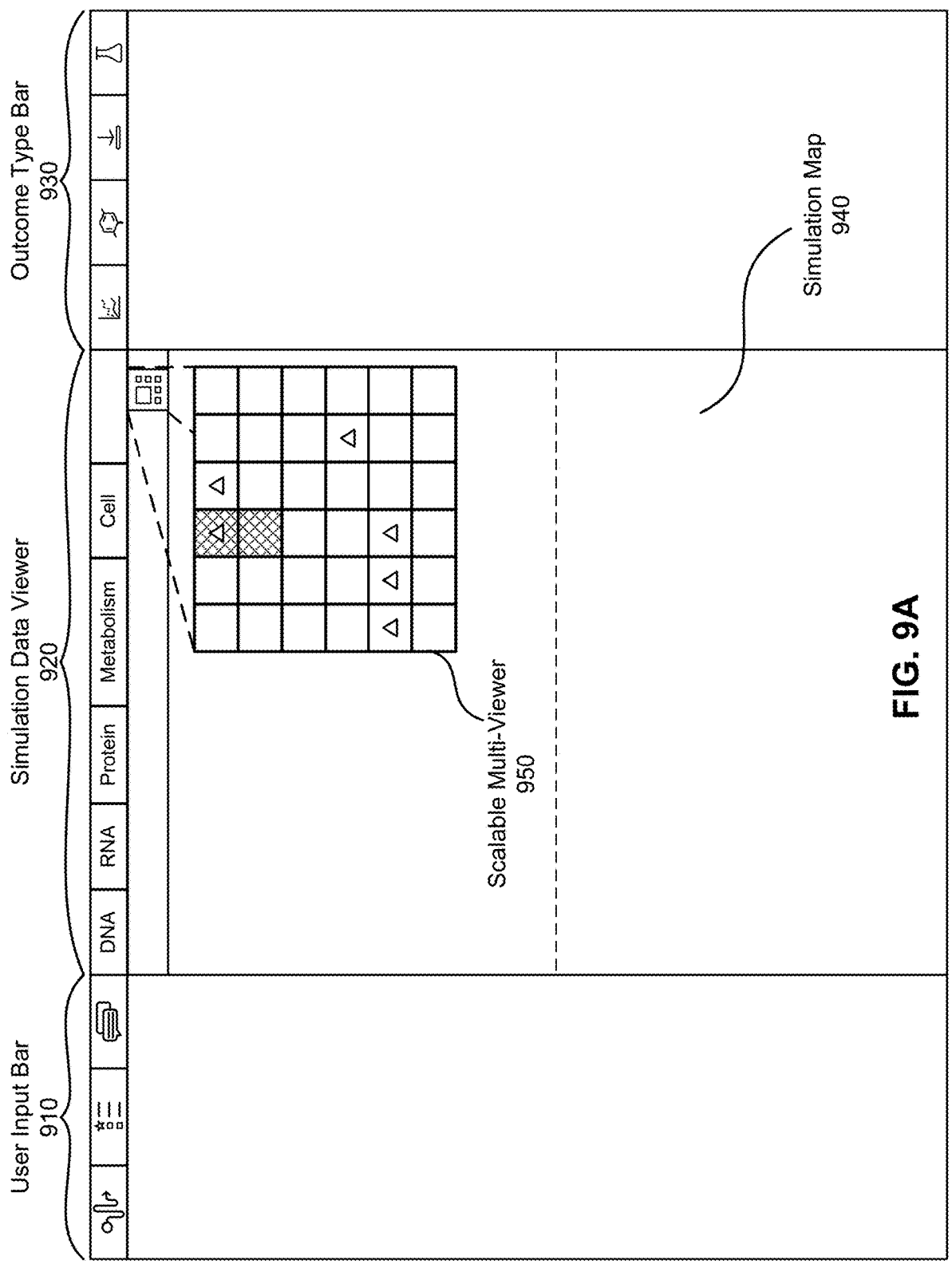
FIG. 9A is an illustration of a graphical user interface of the simulation system, in accordance with an embodiment.

FIG. 9A is an illustration of a graphical user interface (GUI) 900 of the simulation system, in accordance with an embodiment. The simulation system 100 runs one or more simulations generating a separate set of simulation data per simulation. Collectively, a set of simulations is herein referred to as an "experiment" for convenience. The simulation system presents the simulation data for a simulation in the GUI 900 of the simulation system. The GUI 900 may be displayed through a display device of a computing device, specifically through a web page, an application, or another software or firmware mechanism. The GUI 900 presents a number of graphical elements within the GUI in different portions of a display area of the display device. Each such graphical element presents various pieces of information about the simulation, the reaction network, and simulation data from one or more of the simulations. In one embodiment, the graphical elements of the GUI 900 include a user input bar 910, a simulation data viewer 920, and an outcome type bar 930, each of which is a window in the GUI 900. The user input bar 910 and the outcome type bar 930 will be described further in Sections V.B. and V.C. in conjunction with FIGS. 13A-13C and FIGS. 14A-14D, respectively.

The simulation data viewer 920 includes is a simulation map 940 and a scalable multi-viewer 950. The simulation map 940 is a graphical element which visually displays molecule and/or reaction nodes of the cell reaction network. In the example embodiment of FIG. 9A, the simulation map 940 occupies only a portion of the screen area allocated to the simulation data viewer 910.

The scalable multi-viewer 950 is another graphical element which comprises a grid of map tiles, wherein each map tile corresponds to a reaction node in the reaction network 200. The scalable multi-viewer 950 displays some of its map tiles as currently being displayed by the simulation map 940. The scalable multi-viewer 950 is configured to respond to inputs receive from a user via an input device (not shown). For example, the scalable multi-viewer 950 may be hidden or shown in response to a received input selection of a button 935. In one embodiment, the scalable multi-viewer 950 occupies a fixed portion of the simulation data viewer 910 similar to the simulation map 940. Alternately the scalable multi-viewer 950 may be of variable size or moved in response to user input.

Figure 9B:
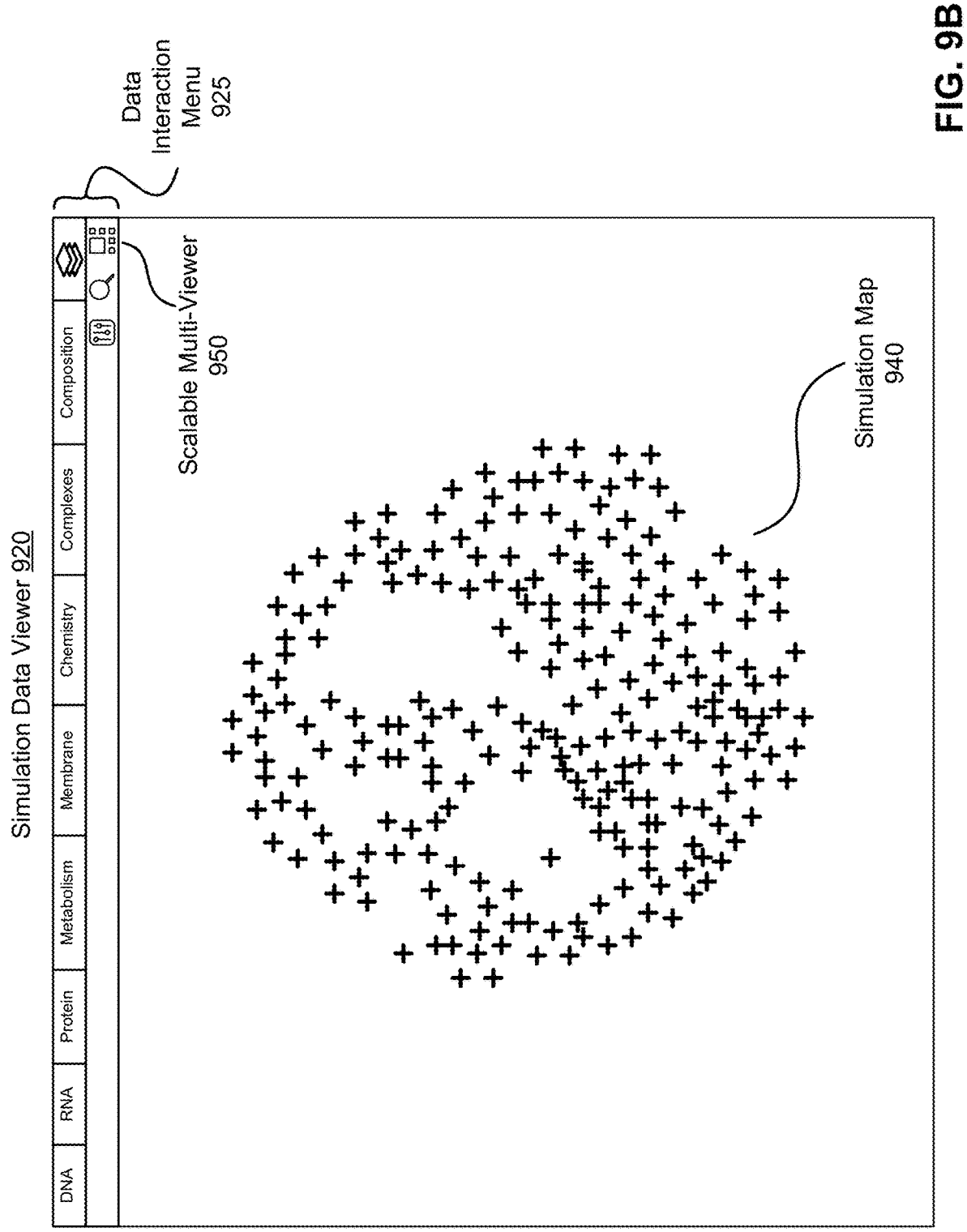
FIG. 9B is an illustration of an example simulation data viewer, in accordance with an embodiment.

FIG. 9B is an illustration of an example simulation data viewer 900, in accordance with an embodiment. The simulation data viewer 900 comprises a simulation interaction menu 925 in addition to the simulation map 940, and the scalable multi-viewer button 935. The simulation interaction menu 925 comprises a plurality of buttons which can present a subset of the simulation data from a simulation according to different focal points. The focal points may be different macro-biological concepts relative to the more granular simulation data provided as output in various forms by the GUI 900. For example, one button can identify all reaction nodes in the cell reaction network that interact with DNA of the biological cell. Another button can present chemical rates of reactions in the cell reaction network.

V.A. Simulation Map and Scalable Multi-Viewer

V.A.I. Overview

Figure 9C:
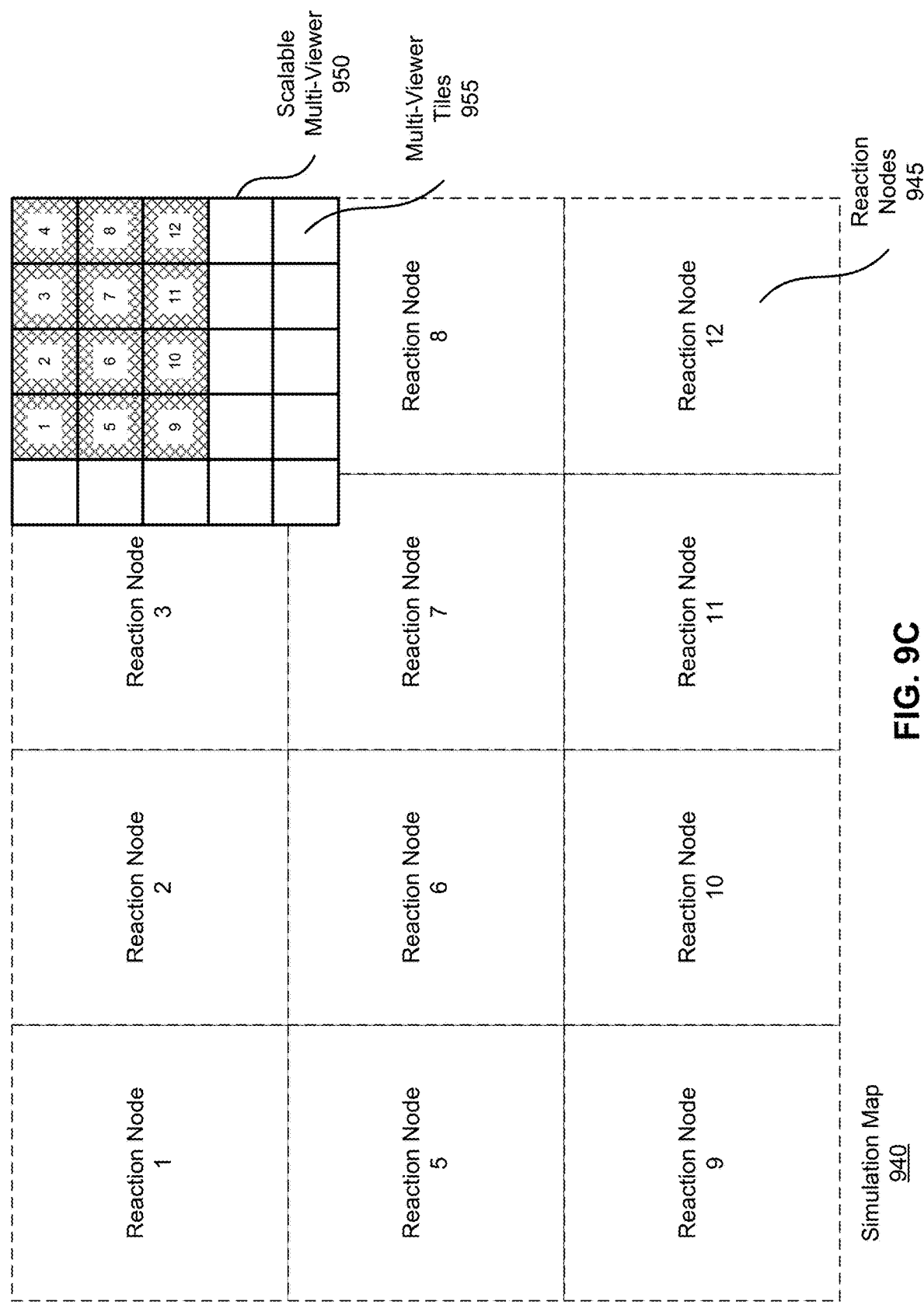
FIG. 9C is a static representation of a simulation map and a scalable multi-viewer, in accordance with an embodiment.

FIG. 9C is a static representation of the simulation map 940 and the scalable multi-viewer 950, in accordance with an embodiment. The simulation map 940 displays a number of reactions nodes 945 arranged in a grid-like arrangement. In this example, twelve such reaction nodes are arranged into three rows and four columns, how the number of nodes, rows, and columns may vary by simulation and based on other factors as detailed below. Similarly, the scalable multi-viewer 950 is also displayed in a grid-like arrangement with a number of multi-viewer tiles 955. At least some of the multi-viewer tiles 955 correspond to the reaction nodes 945 displayed by the simulation map 940. The remaining of the multi-viewer tiles 955 correspond to reaction nodes that are not currently displayed as part of the simulation map 940 by GUI 900, but are in the vicinity of those that are displayed.

In this context, vicinity refers to the relative number of reactions between the reaction nodes currently displayed as part of the simulation map 940 and other reactions (and their corresponding reaction nodes) that are part of the network 200 of cell reactions, either being modeled by a particular model of the simulation or being modeled by any of the models of the simulations. The smaller the number of reactions between a given reaction and a reaction represented by one of the currently displayed nodes, the closer the vicinity and thus the more likely it is that such a reaction is represented by one of the multi-viewer tiles 955 other than those associated with one of the reaction nodes 945 currently displayed by the GUI 900.

In the example of FIG. 9C, twelve of the multi-viewer tiles 955 correspond directly to the reaction nodes 945 in display by the simulation map 940. In this example, the subset of multi-viewer tiles 955 which correspond to the reaction nodes 945 in display are shaded or otherwise visually distinguished so as to ease identification of which multi-viewer tiles are in a field of view of the simulation map 940. Other visual techniques for identification may include drawing a box around the subset and displaying an identifier in each multi-viewer tile in the subset. Those of skill in the art will appreciate other similar ways of distinguishing the subset of tiles.

V.A.II. Zoom

Figure 9D:
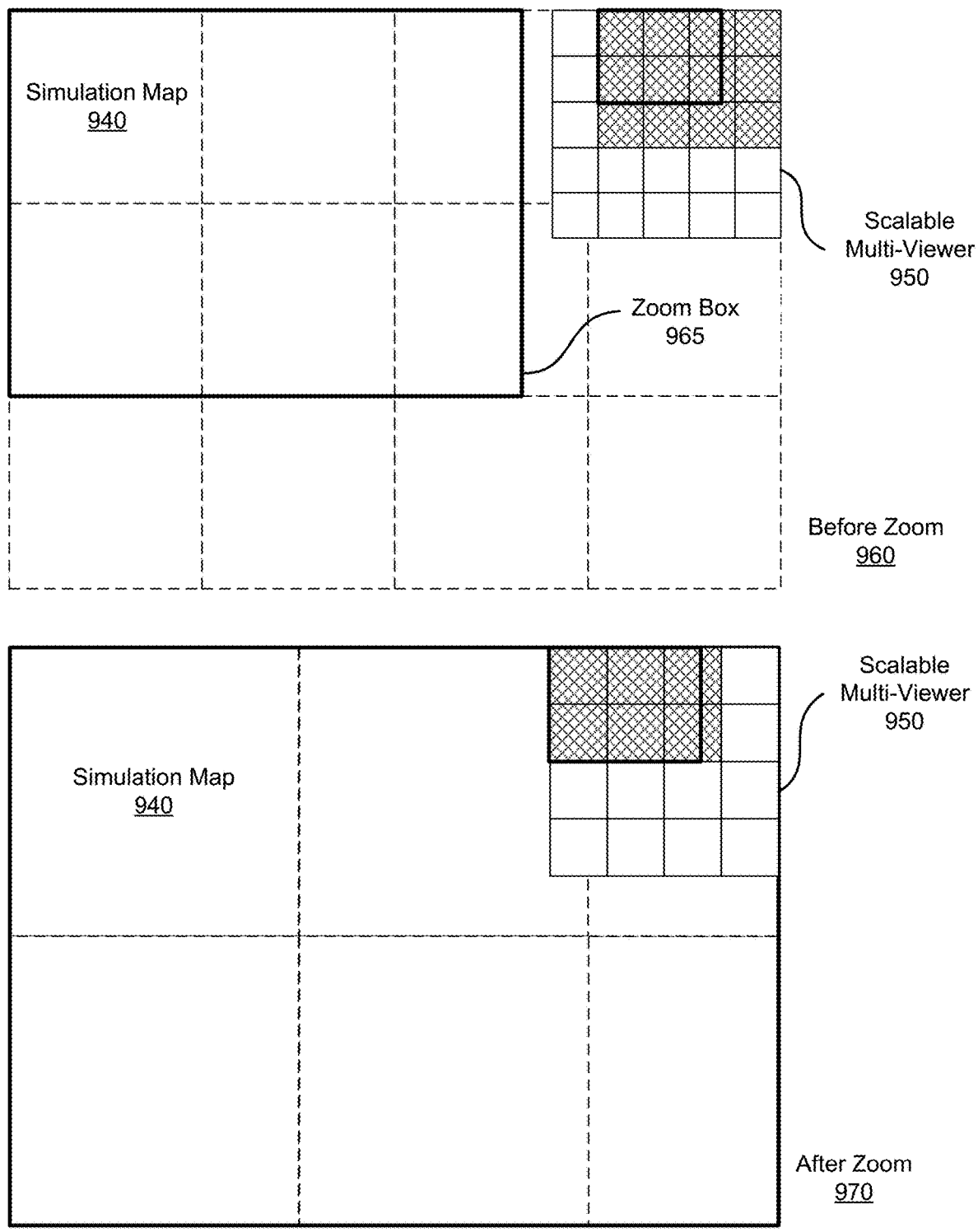
FIG. 9D is a dynamic representation of zooming into the simulation map and the scalable multi-viewer, in accordance with an embodiment.

FIG. 9D illustrates two different views of the simulation map 940 and the scalable multi-viewer 950 in order to illustrate dynamic zooming, in accordance with an embodiment. As shown in the before zoom 960 illustration, in this example the simulation map 940 illustrates twelve reaction nodes 945 currently on display in the GUI 900, and the scalable multi-viewer 950 has a grid of 25 multi-viewer tiles 955 with twelve of the twenty five marked as the current field of view of the simulation map 940.

In response to a zoom input, the simulation map 940 adjusts the number of reaction nodes displayed. The zoom input may be received through an input/output device, such as a scroll action received from a touchpad, finger touch, or mouse scroll. In one embodiment, in response to the start of a zoom input, the GUI 900 may present a zoom box 965 identifying the region of the simulation map 940 to be shown at the conclusion of the zoom input. In this example, the zoom box 965 encompasses six of the twelve reaction nodes 945 in display. The zoom box 965 may scale throughout the zoom input as the input shifts to increase or decrease the amount of zoom. In other embodiments, no zoom box 965 is provided in response to zooming inputs.

At the conclusion of the zoom input, the simulation map 940 adjusts the number and size of reaction nodes 945 in display based on the number of reaction nodes 945 contained within the zoom box 965. As shown in the after zoom 970 example illustration, in response to the example zoom input six reaction nodes 945 in the zoom box 965 now fill the simulation map 940. Additionally, the scalable multi-viewer 950 adjusts to reflect the after zoom 970 field of view of the simulation map 940. In this example embodiment, the scalable multi-viewer 950 changes the number of multi-viewer tiles 955, as shown from twenty five multi-viewer tiles 955 to sixteen multi-viewer tiles 955. As the after zoom 970 field of view of the simulation map 940 includes less reaction nodes 945 than the before zoom 960 field of view, the scalable multi-viewer 950 reflects the change by identifying six of its multi-viewer tiles 955 as being in the after zoom 970 field of view, rather than the twelve prior to the zoom input.

Although the description of FIG. 9D is in relation to a zoom-in input, the same principles apply for a zoom-out input. In one embodiment, for zoom-out zoom inputs, the simulation map 940 and scalable multi-viewer 950 are further configured to dynamically scale during the zoom input. Additionally, the zoom box 965 may grow (or shrink) during the zoom input to reflect the adjustment by the simulation map 940 and the scalable multi-viewer 950 to encompass more reaction nodes 945 and multi-viewer tiles 955. This allows the resulting view of the scalable multi-viewer 950 and the simulation map 940, to show as many reaction nodes as desired in response to the zoom input.

V.A.III. Within-Reaction Node View

Figure 9E:
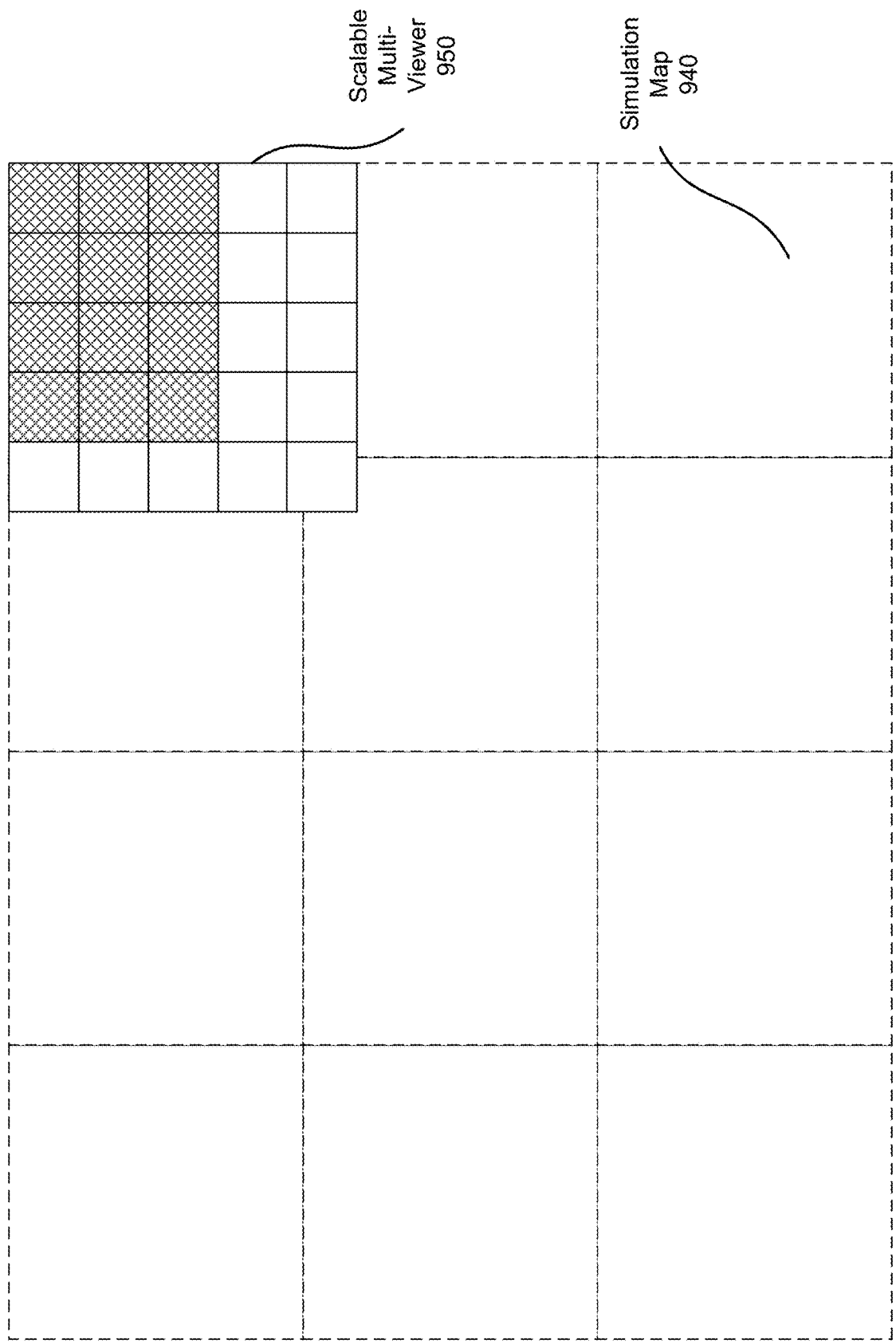
FIG. 9E-9G are illustrations of relatively zoomed-in views of a few of the reaction nodes of the simulation map alongside a concurrently displayed scalable multi-viewer, in accordance with various embodiments.
Figure 9F:
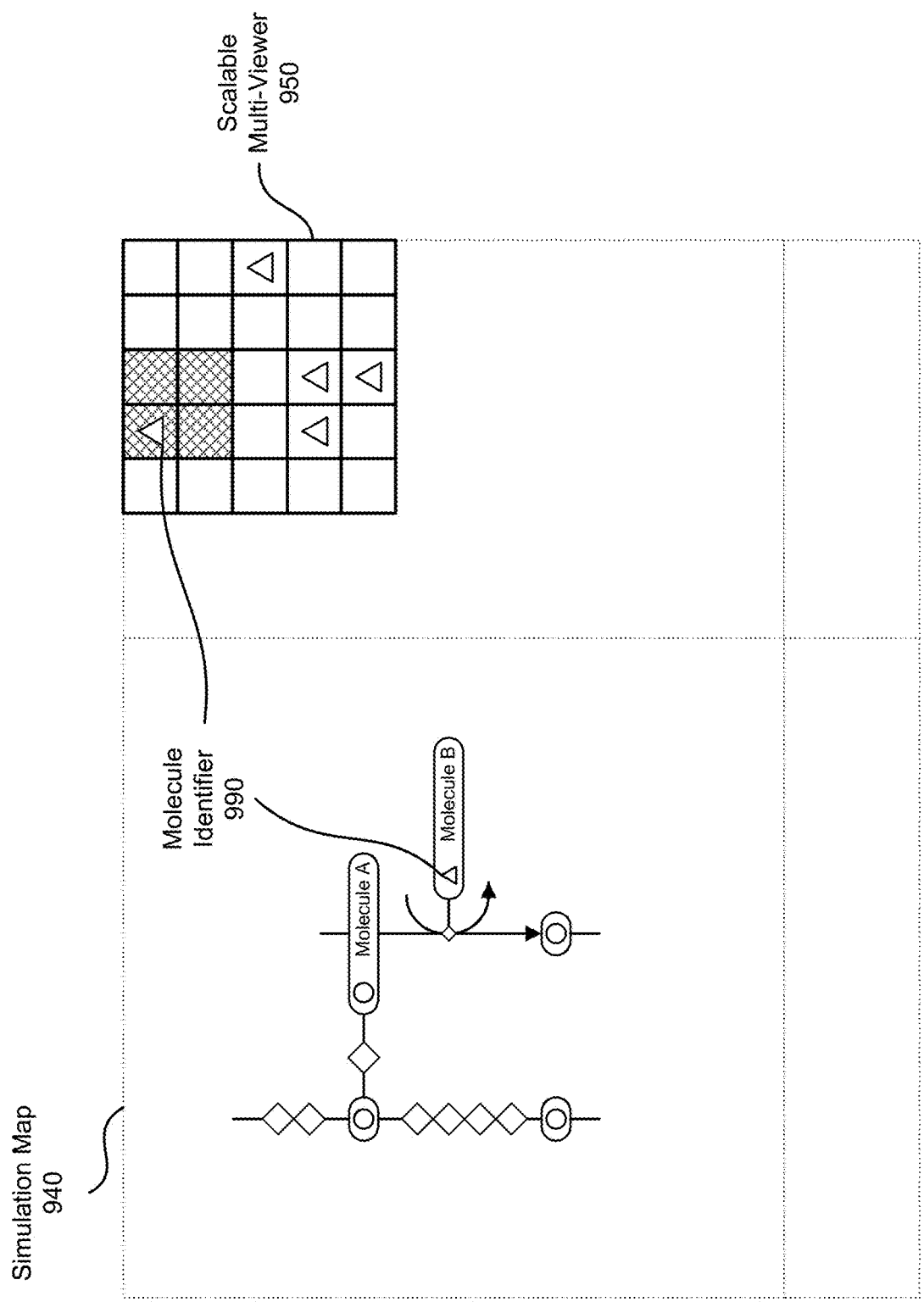
Figure 9G:
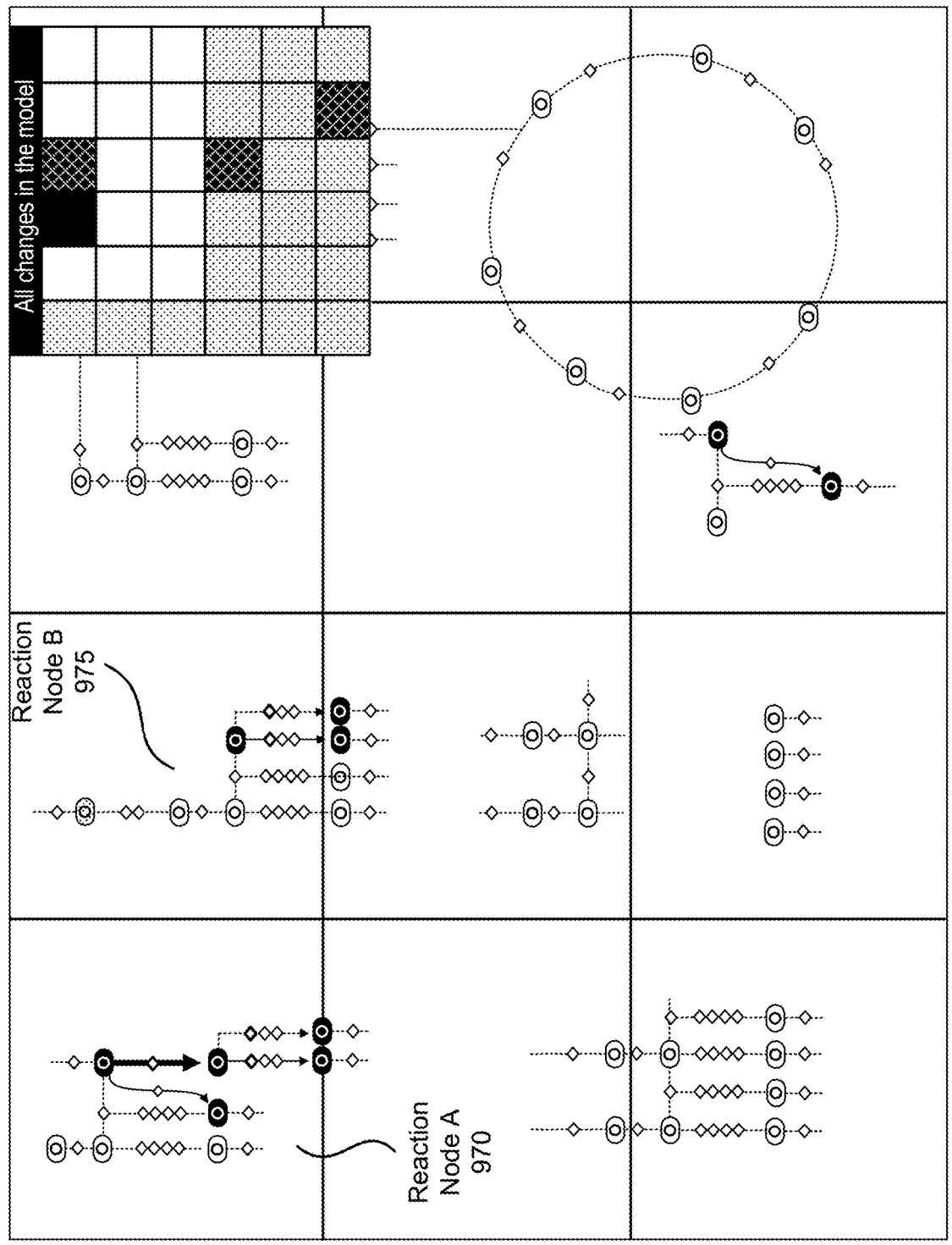

FIG. 9E-9G are illustrations of relatively zoomed-in views of a few of the reaction nodes of the simulation map 940 alongside a concurrently displayed scalable multi-viewer 950, in accordance with various embodiments. A function of the simulation map 940 and scalable multi-viewer 950 is to present for display individual reaction nodes of the simulation map 940, where the reaction nodes each illustrate a particular reaction within network 200, along with the input and output molecules involved in the reaction. Graphical indicators such as shapes or icons may be used to identify and distinguish the different molecules and reactions in the field of view (particularly in the case where more than one reaction node is displayed within the simulation map 940 concurrently). As seen in FIG. 9F, a portion of an example reaction is displayed in a reaction node of the simulation map 940. In the reaction, two molecules are listed, Molecule A and Molecule B, denoted by a circle and a triangle, respectively. In this illustration, reaction node A 970 and reaction node B 975 both contain Molecule B. The circle and the triangle are molecule identifiers for each of the two molecules shown. Displaying molecule identifiers in the scalable multi-viewer 950 provides a visual aid to a user of the GUI 900. The user can easily identify other reaction nodes outside a current field of view of the simulation map 940 which contains a selected molecule. The user can then quickly access other reaction nodes containing the selected molecule as relative locations of the other reaction nodes can be perceived through the scalable multi-viewer 950. FIG. 9G shows alternate examples of how the simulation map 940 may depict the contents of reaction nodes, specifically illustrating visual depictions of edges connecting process and molecule nodes from the reaction network 200.

In response to a user input selecting a molecule, the scalable multi-viewer 950 can access and display information regarding surrounding reaction nodes in the reaction network 200 that also interact with Molecule B. In one embodiment, the scalable multi-viewer 950 displays a molecule identifier 990 in each multi-viewer tile having a reaction node that interacts with Molecule B. The molecule identifier 990 used in the multi-viewer tiles is the same identifier displayed and selected in the simulation map 940 for ease of user understanding. However, in alternate embodiments, other graphical representations may be used. User inputs may be received to select more than one molecule. In response, the scalable multi-viewer 950 can display multiple such identifiers, one for each of the selected molecules for each reaction node interacting with one or more of the selected molecules (not shown). This can be useful in considering whether two molecules appear frequently in reaction nodes of the cell reaction network. In an alternate embodiment, the scalable multi-viewer 950 displays an identifier for only reaction nodes which interact with both/all selected molecules.

V.A.IV. Simulation Map Presenting Simulation Data

Figure 10:
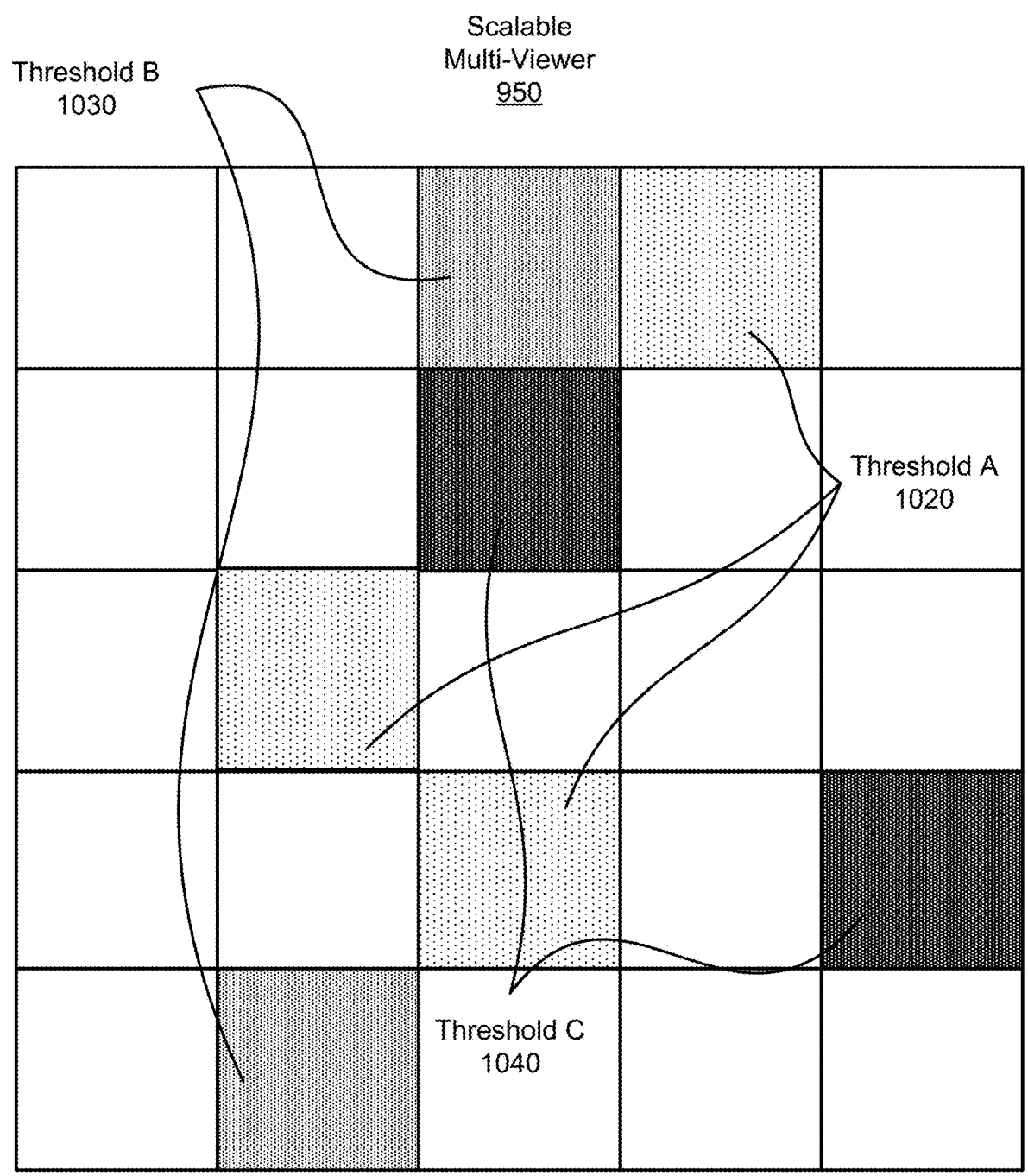
FIG. 10 is an illustration of the scalable multi-viewer identifying reaction nodes with varying differentials compared to a baseline cell state, in accordance with an embodiment.

FIG. 10 is an illustration of the scalable multi-viewer 950 illustrating reaction nodes with varying quantities or differentials compared to a baseline cell state, in accordance with an embodiment. Another function of the scalable multi-viewer 950 is to display aspects of the simulation data that are of value to the user, and in such a fashion so as to make it easier for them to draw insights from the simulation data.

One specific example is that the scalable multi-viewer 950 may display end-of-simulation quantities of molecules obtained from the simulation data or differentials between end-of simulation quantities and a baseline cell state. Similar calculations may be determined based on numbers of reactions that occurred, or reaction rates during or over the course of the simulation. As described earlier, the baseline cell state can be a control simulation as defined in the experiment, or the state of the cell prior to the simulation. The simulation data can be compared against the baseline cell state, and differentials calculated between the simulation data and that of the baseline. One calculation simply takes differences between simulation data and baseline data. Another calculation takes a ratio of simulation data to the baseline data. In an example of the former calculation, data differentials can be calculated by taking the difference between reaction rates from the simulation data and the baseline data for a given reaction.

Accessing these quantities and/or rates, scalable multi-viewer 950 identifies reaction nodes and corresponding multi-viewer tiles 955 with quantities, reaction rates, or differentials thereof that surpass one or more tiered thresholds. The scalable multi-viewer 950 visually distinguishes its displayed multi-viewer tiles 955 depending on which thresholds the corresponding reaction nodes exceeded during the simulation. The user may observe and further delve into sections of the scalable multi-viewer 950 that are visually distinguished due to being above threshold differentials.

FIG. 10 shows an example of the incremental thresholds for a quantity differential versus baseline where there are three total thresholds—threshold A 1020, threshold B 1030, and threshold C 1040. In this example, threshold A 1020 is smaller than threshold B 1030 which is smaller than threshold C 1040. Accordingly, the lightly shaded multi-viewer tiles 955 correspond to reaction nodes that at least surpass threshold A 1020. The scalable multi-viewer 950 uses a medium shade to display multi-viewer tiles corresponding to reaction nodes that also surpass threshold B 1030. Lastly, the scalable multi-viewer 950 uses the darkest shade to distinguish multi-viewer tiles 955 corresponding to reaction nodes that surpass threshold C 1040.

Presented by the scalable multi-viewer 950, a user can easily distinguish reaction nodes which resulted in little to no effect or change for a given molecule or reaction, thereby ignoring them. Likewise, a user can distinguish varying degrees of effect for a given molecule or reaction, thereby drawing their attention to what aspects of the reaction network 200 were more heavily affected by the simulation's parameters. Presented in this way, a contemplated use case is that having been provided with information about what reactions and/or molecules were affected by the simulation, the user will provide and the GUI 900 will receive a zoom input to zoom in on those reaction nodes of interest to the user that experienced significant change in a simulation. The user can then view the molecules and reactions of interest (for example, as illustrated in FIG. 9F) to gain more insight into the underlying biological processes. Through user selection of individual reactions and compounds, the GUI 900 can provide linking information via icons or similar to other reaction nodes that interact with selected reactions and/or molecules, providing the user insight into how possible changes to selected molecules or reactions (e.g., through the introduction of a drug) would affect other parts of the reaction network 200. Additionally, the user may adjust simulation parameters of a subsequent simulation to further study the molecules and reactions with significant change.

V.A.V. Connectors

Figure 11:
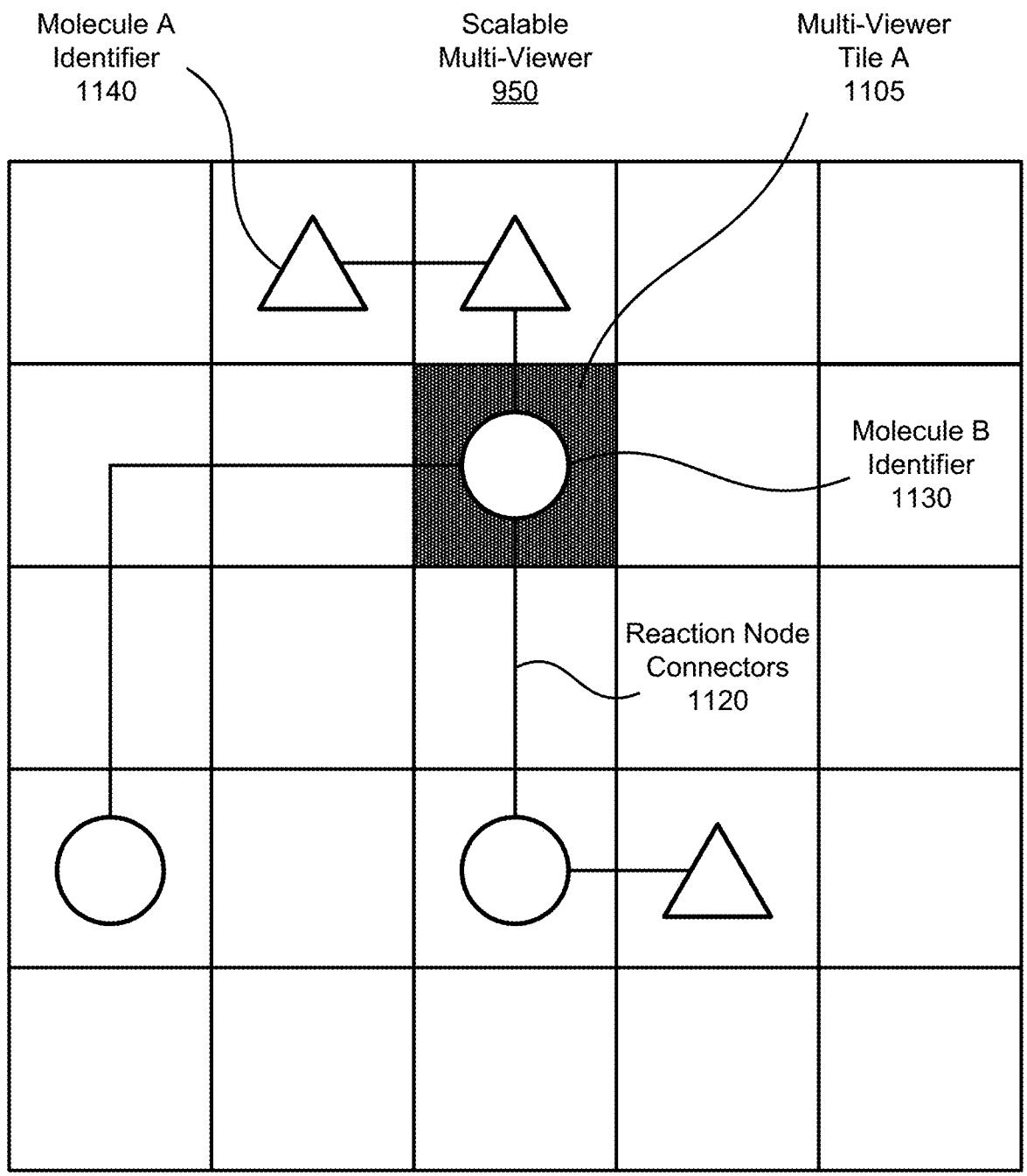
FIG. 11 is an illustration of the scalable multi-viewer identifying edges between reaction nodes and related molecules, in accordance with an embodiment.

FIG. 11 is an illustration of the scalable multi-viewer 950 displaying connectors between reaction nodes 945 and related molecules, in accordance with an embodiment. Another function of the scalable multi-viewer 950 is displaying connectors between various reaction nodes 945 in the cell reaction network 200. As introduced above, each reaction node in the cell reaction network 200 may be indirectly coupled to a number of reaction nodes through its input and output molecules. These upstream and downstream reactions (and molecules) may be of interest to a user. For example, per the description above if a simulation has identified that a particular reaction or molecule has changed significantly as a result of a simulation, upstream and downstream reactions and molecules may be of interest to a user. The scalable multi-viewer 950 is able to provide such information in an easily interpretable manner.

In response to receiving a user input selecting a multi-viewer tile 955, the scalable multi-viewer 950 displays one or more connectors between the selected multi-viewer tile and one or more other multi-viewer tiles. In one implementation, the scalable multi-viewer 950 may connect multi-viewer tiles corresponding to reaction nodes which relate to the selected reaction node. Additionally, the scalable multi-viewer 950 may present information related molecules or compounds along with the connectors. In an alternate embodiment, the scalable multi-viewer displays the connectors in response to a user input selecting a reaction node 945 in the simulation map.

FIG. 11 illustrates an example of the prior paragraph. In the example of FIG. 11, the scalable multi-viewer 950 responds to an input selecting a multi-viewer tile A 1105. In one embodiment, the scalable multi-viewer 950 visually distinguishes the selected multi-viewer tile so that the user is aware of which multi-viewer tile 955 is causing the connectors to be shown. The scalable multi-viewer 950 accesses the reaction network 200 to identify reaction nodes related to the reaction node corresponding to the selected multi-viewer tile A 1105. The scalable multi-viewer 950 displays connectors 1120 from the reaction node 1105 to the other reaction nodes identified from the reaction network 200 to be related to the reaction node 1105. In the example of FIG. 11, there are three branches of connectors 1120 stemming from the multi-viewer tile A 1105. The scalable multi-viewer 950 also identifies other reaction nodes that are connected to the reaction node 1105 that also interact with molecule B by placing a molecule B identifier 1130—demarcated as a circle. Similarly, the scalable multi-viewer 950 accesses the reaction network 200 to identify reaction nodes 945 in the reaction network 200 which could are connected to a molecule B which is connected to the selected multi-viewer tile 1105. The scalable multi-viewer 950 displays connectors to those reaction nodes 945 connected to the reaction node 1105 that interact with molecule A by placing a molecule A identifier 1140—demarcated as a triangle.

Displaying connectors between molecules of interest involved in reactions within the scalable multi-viewer 950 allows for a user to more easily follow the connections between reactions and molecules in the reaction network 200, and obtain information about the consequences inquiry into a specific reaction node or a specific molecule. The connectors 1120 provide guidance in relating reaction nodes in the vast cell reaction network 200. Continuing with the example discussed previously, if the reaction node associated with multi-viewer tile A 1105 was indicated as having a significant change in a quantity or rate as indicated by the example FIG. 10, FIG. 11 then represents a use case where a user input has been received to select multi-viewer tile A 1105 to obtain more information about related reactions and molecules. FIG. 11 facilitates the user's ability to obtain this information for displaying this information as part of the multi-viewer, without necessarily forcing them to zoom in to the simulation map 940 as illustrated, for example, in FIGS. 9C, 9D, and 9E to obtain this information. Thus, the GUI 900 presents simulation data in multiple different ways and at different levels of granularity, and is easily manipulable to obtain this information quickly, allowing more efficient navigation of what is often significant quantities of output simulation data.

V.A.VI. Regions of Interest

Figure 12:
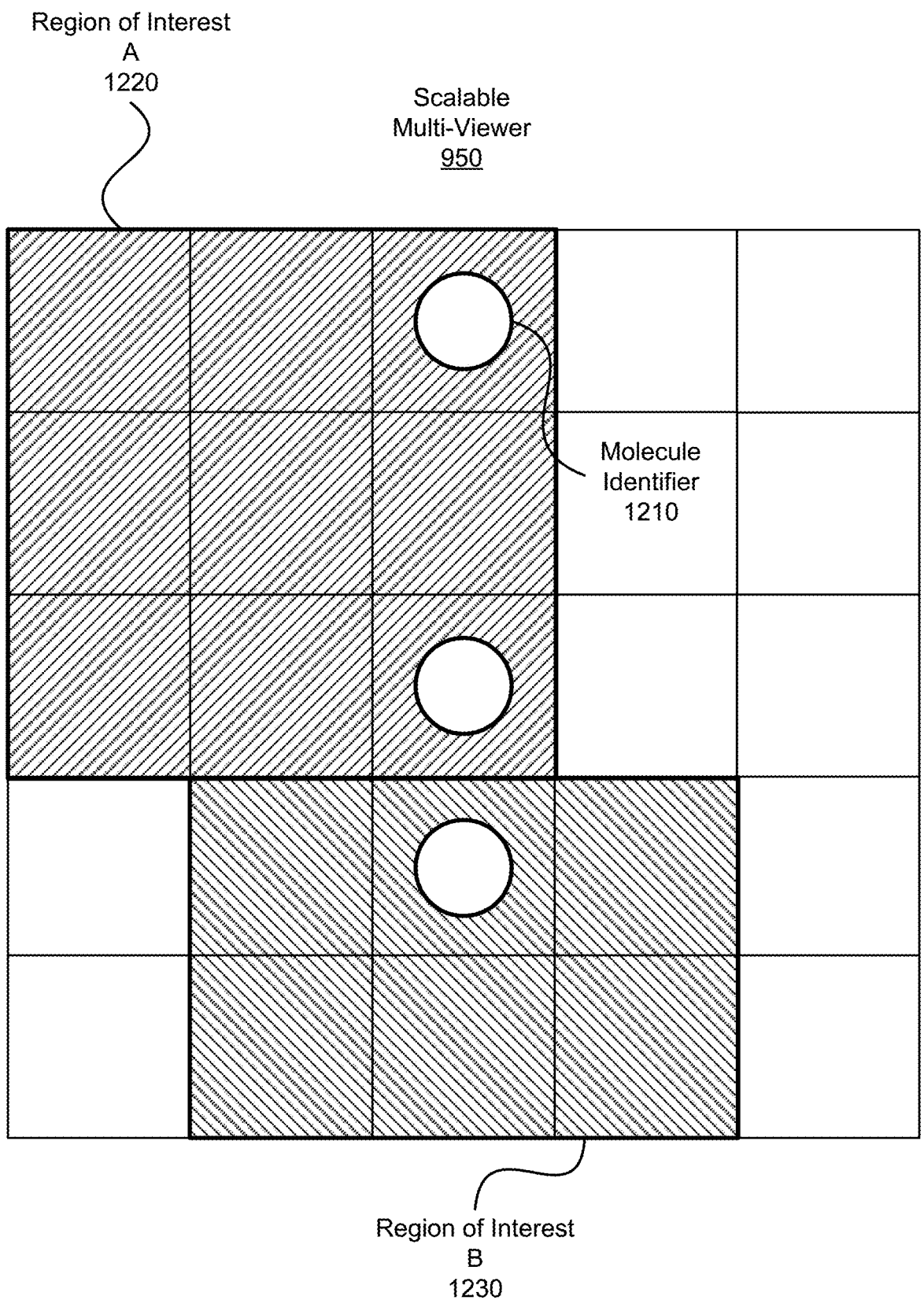
FIG. 12 is an illustration of the scalable multi-viewer identifying regions of interest within the simulation map, in accordance with an embodiment.

FIG. 12 is an illustration of the scalable multi-viewer 950 displaying regions of interest within the simulation map 940, in accordance with an embodiment. Another function of the scalable multi-viewer 950 is displaying in a visually distinguished manner particular reaction nodes that share a common aspect. In one embodiment, the GUI 900 may receive a user input selecting a molecule or reaction of interest, and a macromolecular influence of interest. Using the example FIG. 12, the GUI 900 may receive a user input selecting an enzyme current displayed by one of the multi-viewer tiles. The GUI 900 may further receive a user input selecting an RNA influence on the enzyme. Generally, in response to these selections, the scalable multi-viewer 950 displays multi-viewer tiles with a visual identifier, such as the circle 1210 in FIG. 12, corresponding to reaction nodes of the displayed multi-viewer tiles 955 including the selected molecule of interest. Additionally, the scalable multi-viewer 950 visually distinguishes multi-viewer tiles 955 associated with reaction nodes related to the selected macromolecular influence on the selected molecule of interest. In FIG. 12, this is illustrated as cross hatching. As often these associated reaction nodes adjoin or are in close relative vicinity to each other (as described above) within reaction network 200, this visual indication will appear as whole regions being identified, herein referred to as regions of interest. More than one macromolecular influence may be represented visually in the scalable multi-viewer 950 simultaneously. In the example of FIG. 12, region of interest A 1220 corresponds to one macromolecular influence (e.g., DNA) with the molecule and region of interest B 1230 corresponding to another macromolecular influence (e.g., RNA, protein, metabolism).

Any combination of the various additional functions described in FIGS. 10-12 can be implemented with the zooming function described in FIGS. 9C & 9D. Similarly, any combination of the principles described in FIGS. 9C, 9D, 9E, and 10-12 can be used for identifying various portions of simulation data from multiple simulations simultaneously.

V.B. User Input Bar

Figure 13A:
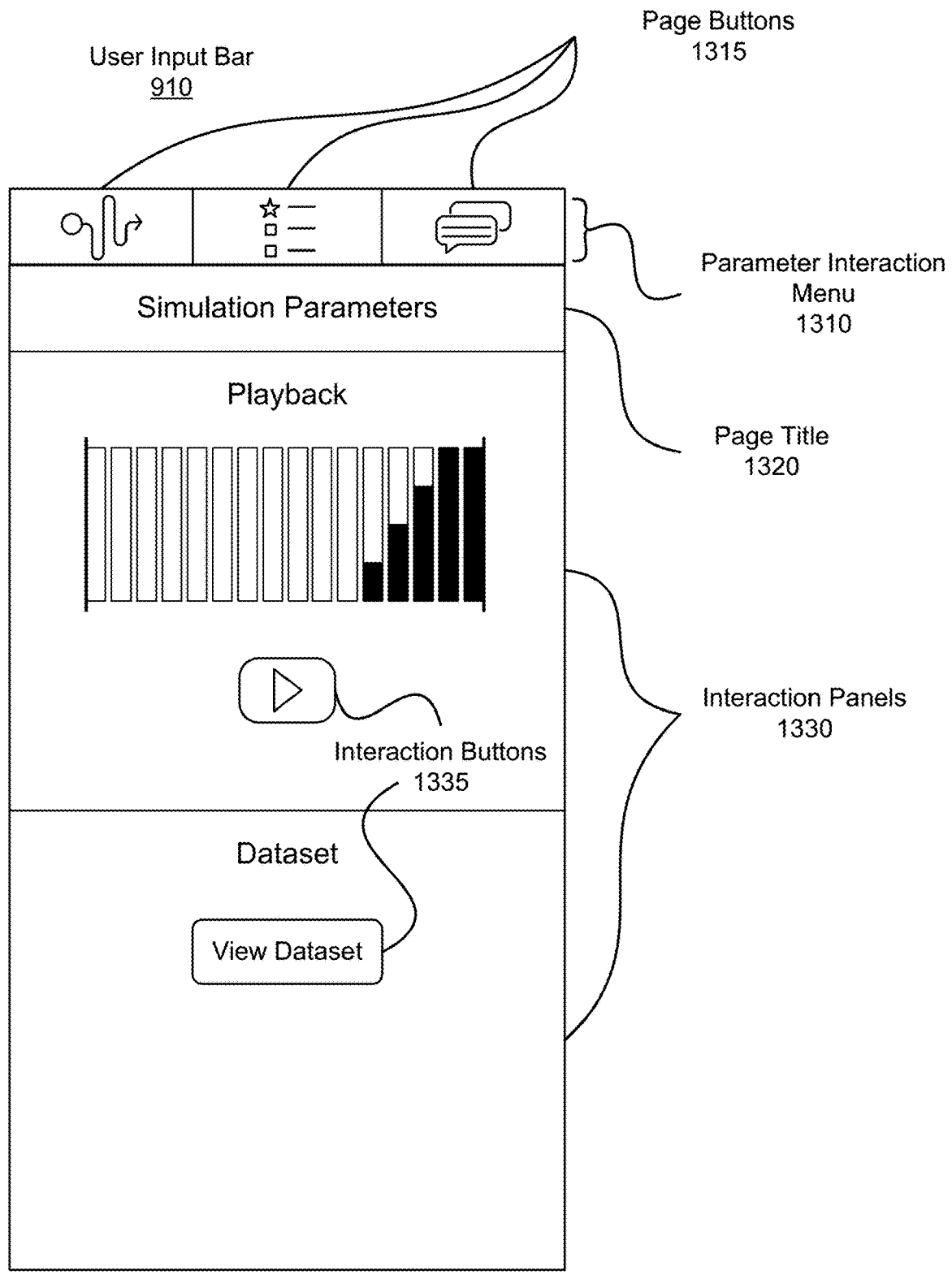
FIG. 13A-C are illustrative examples of the user input bar, in accordance with an embodiment.

FIG. 13A is an illustration of a user input bar 910, in accordance with an embodiment. In this example embodiment, the user input bar 910 comprises a parameter interaction menu 1310, a page title 1320, a plurality of interaction panels 1330, and a plurality of interaction buttons 1335. The parameter interaction menu 1310 comprises a plurality of page buttons 1315 for quickly selecting between a variety of functions. In one embodiment, the parameter interaction menu 1310 includes a page button for toggling simulation parameters, another page button for accessing previous run experiments and/or specific simulations, and another page button for accessing threads of comments between collaborators on particular experiments and/or simulations. As a user selects a page button from the parameter interaction menu 1310, the user input bar 910 changes the page title 1320 as well as content displayed in the interaction panels 1330. Additionally, in response to a user input selecting a page, the user input bar 910 may visually distinguish the selected page or the currently displayed page. The user input bar 910 facilitates navigation around various functions for interacting with the simulation data.

In the illustration of FIG. 13A, the GUI 900 receives a user input selecting the page for toggling simulation parameters. In response, the user input bar 910 displays the page title 1320 corresponding to the page for toggling simulation parameters. The interaction panels 1330 associated with simulation parameters each display one or more parameters for tuning a simulation or an experiment. In one interaction panel 1330, one or more buttons 1335 prompt a user to provide input for an experiment or a simulation in an experiment. In another interaction panel 1330, a button starts a simulation. Another button 1335 may replay a simulation after the simulation has been run as displayed in FIG. 13A. In replaying a simulation, a user may define, via the buttons 1335, a threshold differential between simulation data and baseline data. The simulation can be partitioned into time intervals wherein the average differential between simulation data and baseline data is calculated over the time interval. As the playback commences, the simulation map 940 can highlight regions of the cell reaction network which surpass the threshold differential. As the playback continues, the simulation map 940 adjusts the highlighted regions at each interval. In an alternate embodiment, the simulation map 940 is a color map with the color spectrum mapping to differentials between the simulation data and the baseline data, such that the simulation map 940 adjusts coloration of regions in view of the simulation data over time. Another interaction panel 1330 can have a button 1335 for viewing the dataset.

Figure 13B:
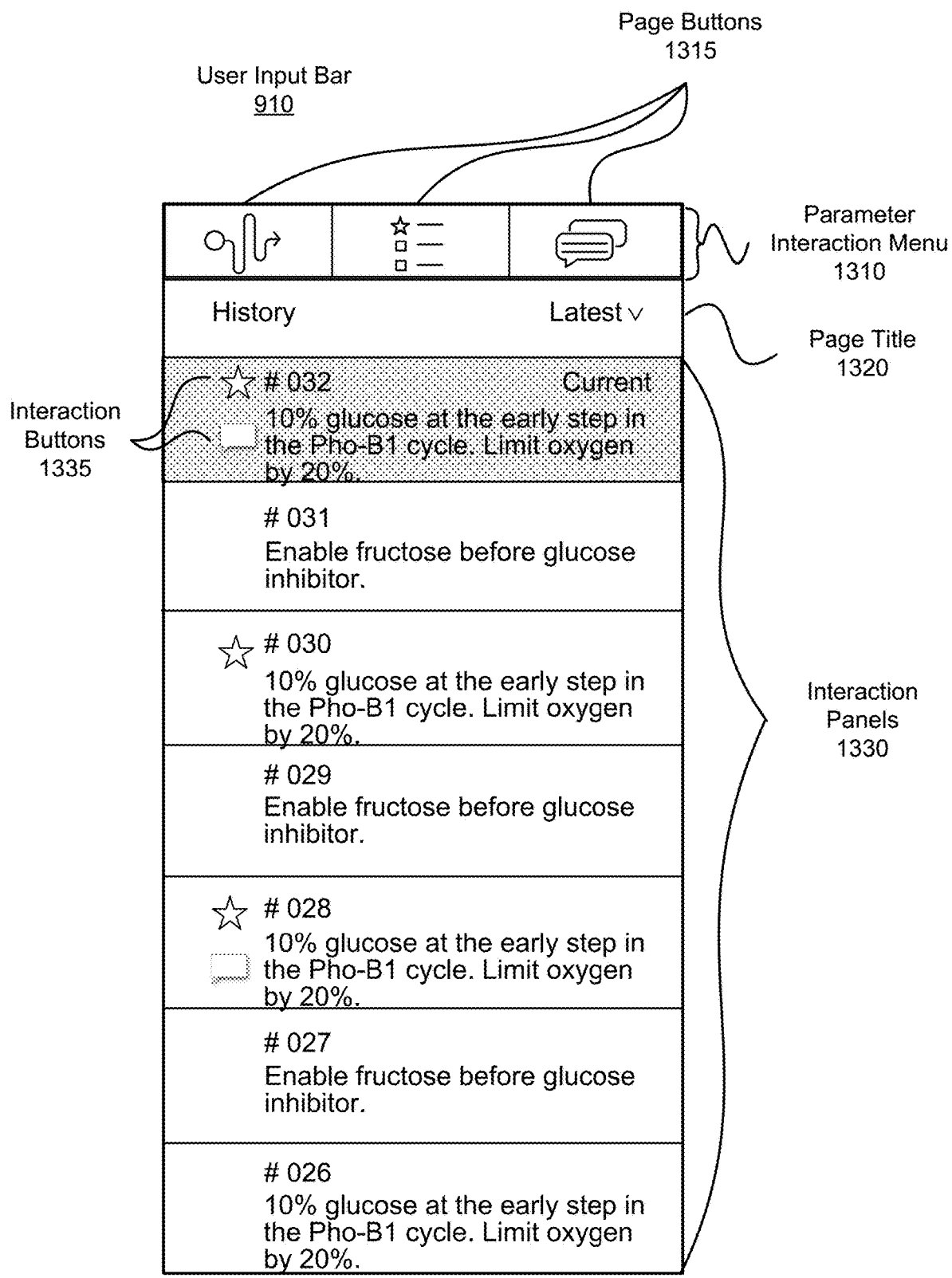

In one embodiment in FIG. 13B, the user input bar 910 receives a user input selecting the page for accessing previous run experiments or simulations. In response, the user input bar 910 displays the page title 1320 corresponding to that page (e.g. "History"). The interaction panels 1330 can each display past simulations or experiments. The buttons 1335 allow a user to select multiple simulations or experiments for comparison with the current simulation. The user input bar 910 may further receive a user input from the buttons 1335, to which the user input bar 910 visually distinguishes the selected simulations or experiments. In this illustration, the user input bar 910 displays a star next to selected simulations.

Figure 13C:
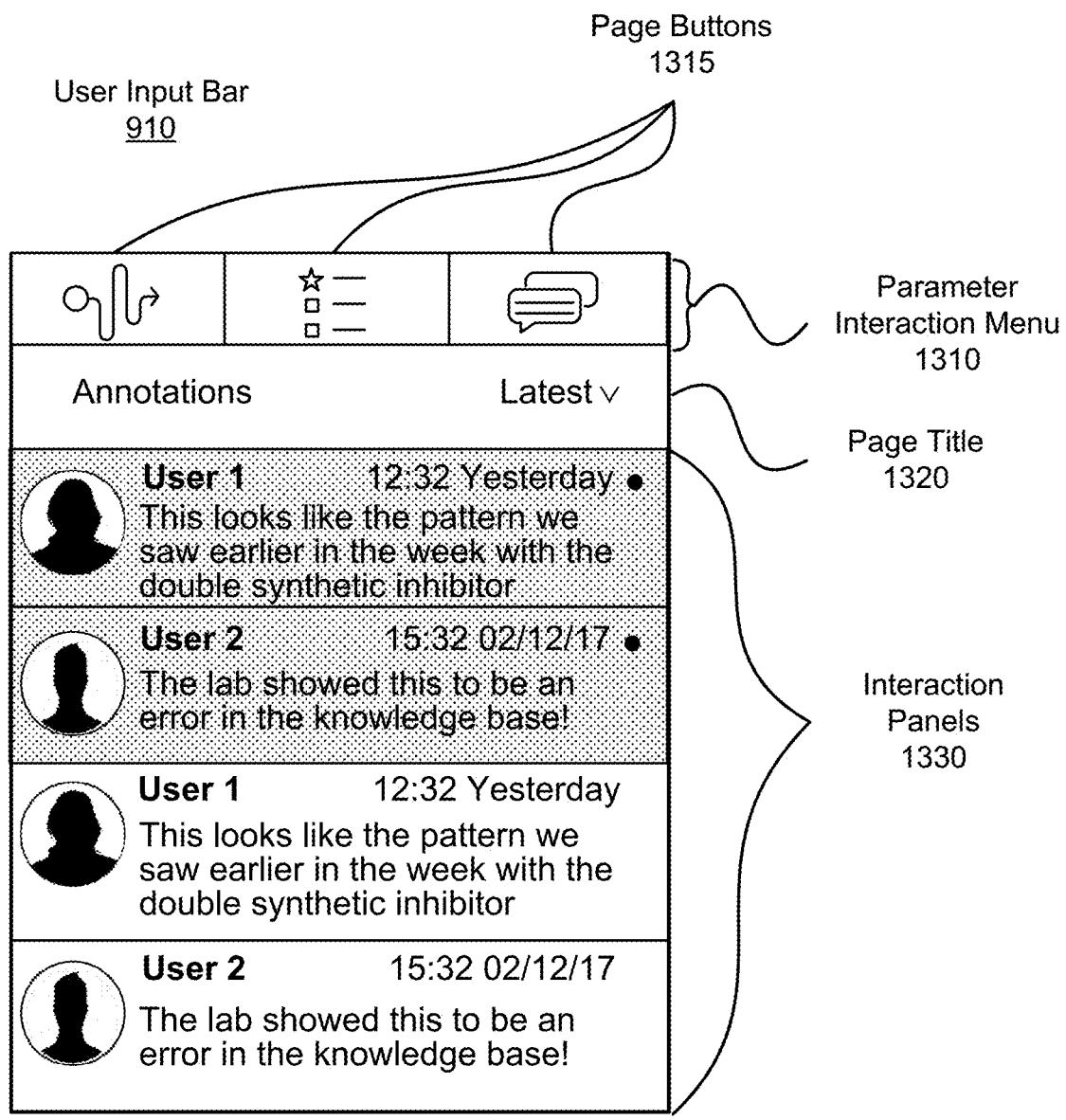

In one embodiment in FIG. 13C, the user input bar 910 receives a user input selecting the page for accessing threads of comments between collaborators. In response, the user input bar 910 displays the page title 1320 corresponding to that page (e.g. "Annotations"). The interaction panels 1330 can each display a comment thread. The user may select a comment thread and input a response onto the comment thread.

V.C. Outcome Type Bar

Figure 14A:
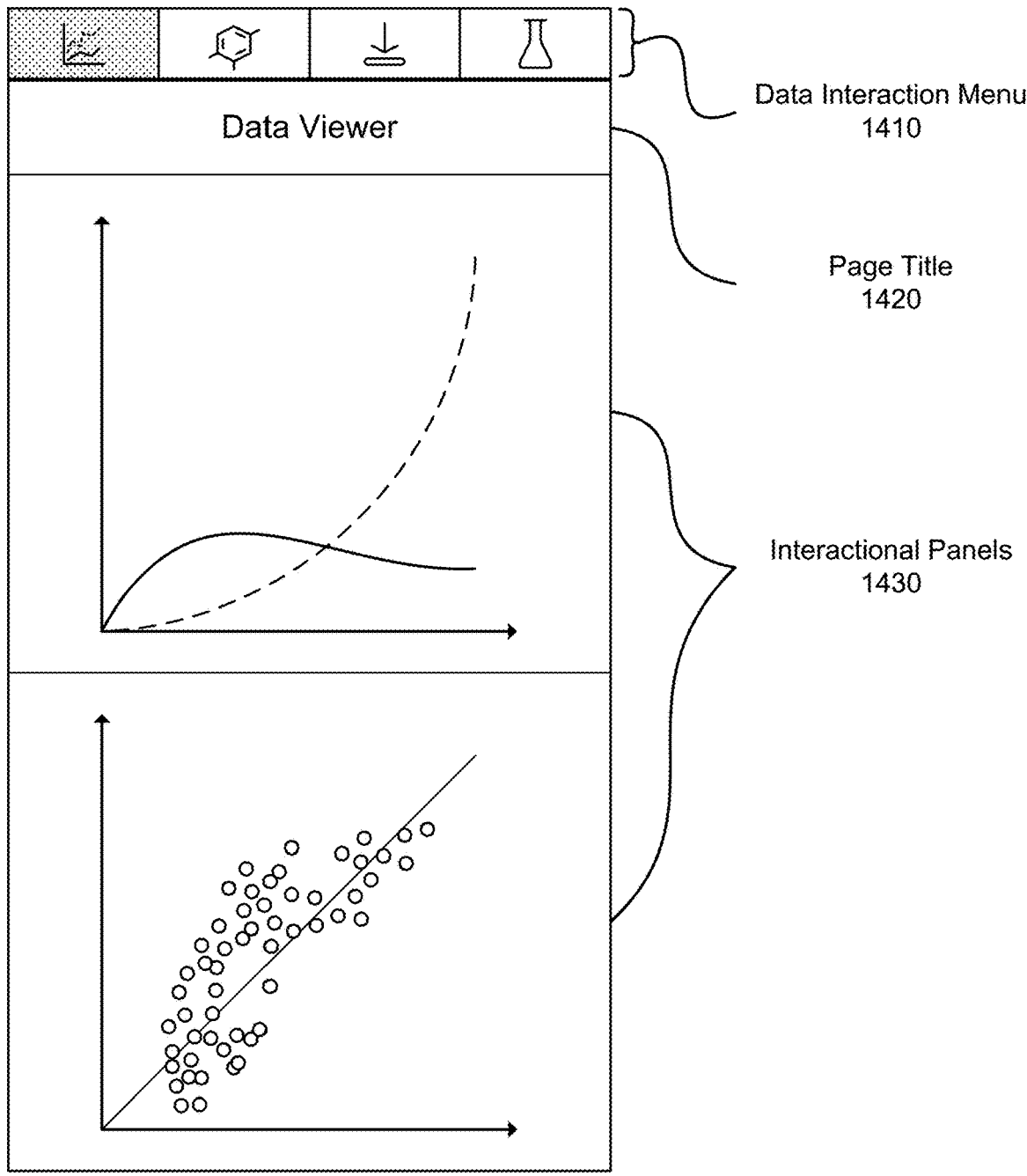

FIG. 14A is an illustration of an outcome type bar 930, in accordance with an embodiment. The outcome type bar 930 comprises a data interaction menu 1410, a page title 1420, and a plurality of interaction panels 1430. In additional embodiments, the outcome type bar 930 comprises buttons similar to those described in FIG. 13A as buttons 1335. The data interaction menu 1410, like the parameter interaction menu 1310, displays a plurality of page buttons for selecting a variety of functions. In one embodiment, the data interaction menu 1410 includes a page button for viewing graphical representations of simulation data, another page button for searching a reference database, another page for downloading or uploading data from the simulation, and another page button for accessing wet lab data. As a user selects a page button from the data interaction menu 1410, the outcome type bar 930 changes the page title 1420 as well as content displayed in the interaction panels 1430. Additionally, in response to a user input selecting a page, the outcome type bar 930 may visually distinguish the selected page or the currently displayed page. Similar to the user input bar 910, the outcome type bar 930 facilitates navigation around various functions for interacting with the simulation data.

In one embodiment in FIG. 14B, the outcome type bar 930 receives a user input selecting the page for searching a reference database. In response, the outcome type bar 930 displays the page title 1420 corresponding to that page (e.g. "Search Database", "Reference"). Additionally the outcome type bar 930 display information retrieved from a referential database. The referential database provides information to a query by the page. In some embodiments, the outcome type bar 930 includes a search input through which the user can search various terms. In other embodiments, the simulation data viewer 920 receives a user input selecting a molecule, a reaction node 945, a multi-viewer tile 955, a macromolecular influence, or etc. In response, the simulation data viewer 920 sends a query the referential database. The outcome type bar 930 then displays the information logged in the referential database in response to the query. Such a display allows the user to, within the same GUI 900 display area that includes the simulation data viewer 920 and user input bar 910 as described with respect to FIG. 14A above, obtain research information regarding specific aspects of the simulation and simulation data set, for example as shown in those other parts of the GUI 900 concurrently.

Figure 14C:
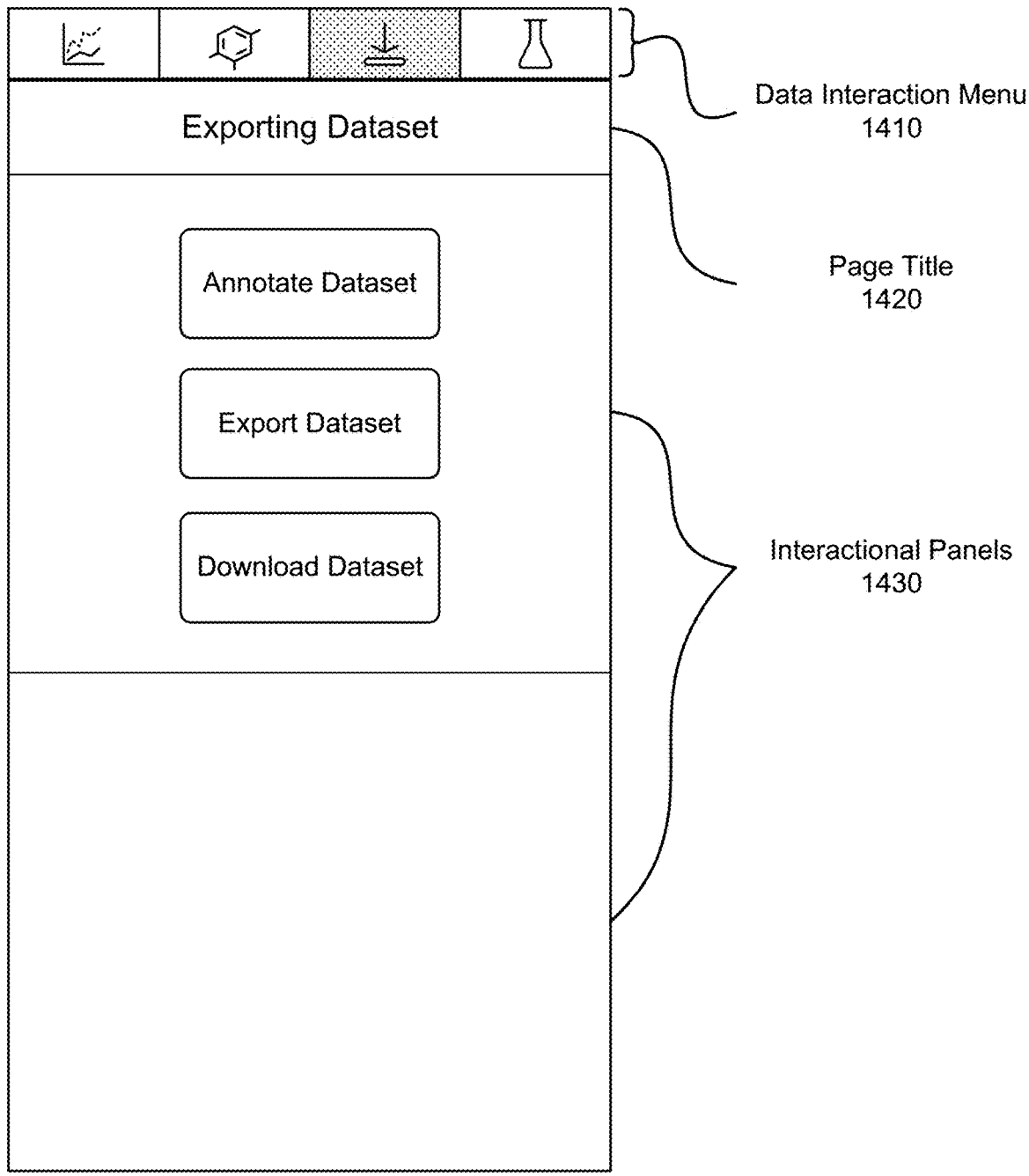

In another embodiment in FIG. 14C, the outcome type bar 930 receives a user input selecting the page for exporting the dataset. In response, the outcome type bar 930 displays the page title 1420 corresponding to that page (e.g. "Exporting Dataset"). Various buttons can allow a user to selectively interact with the data. For example, one button displays the dataset in an editable format. In another example, one button exports the dataset to another application or server. In another example, one button downloads the dataset. This allows for easy export of the dataset by the user.

Figure 14D:
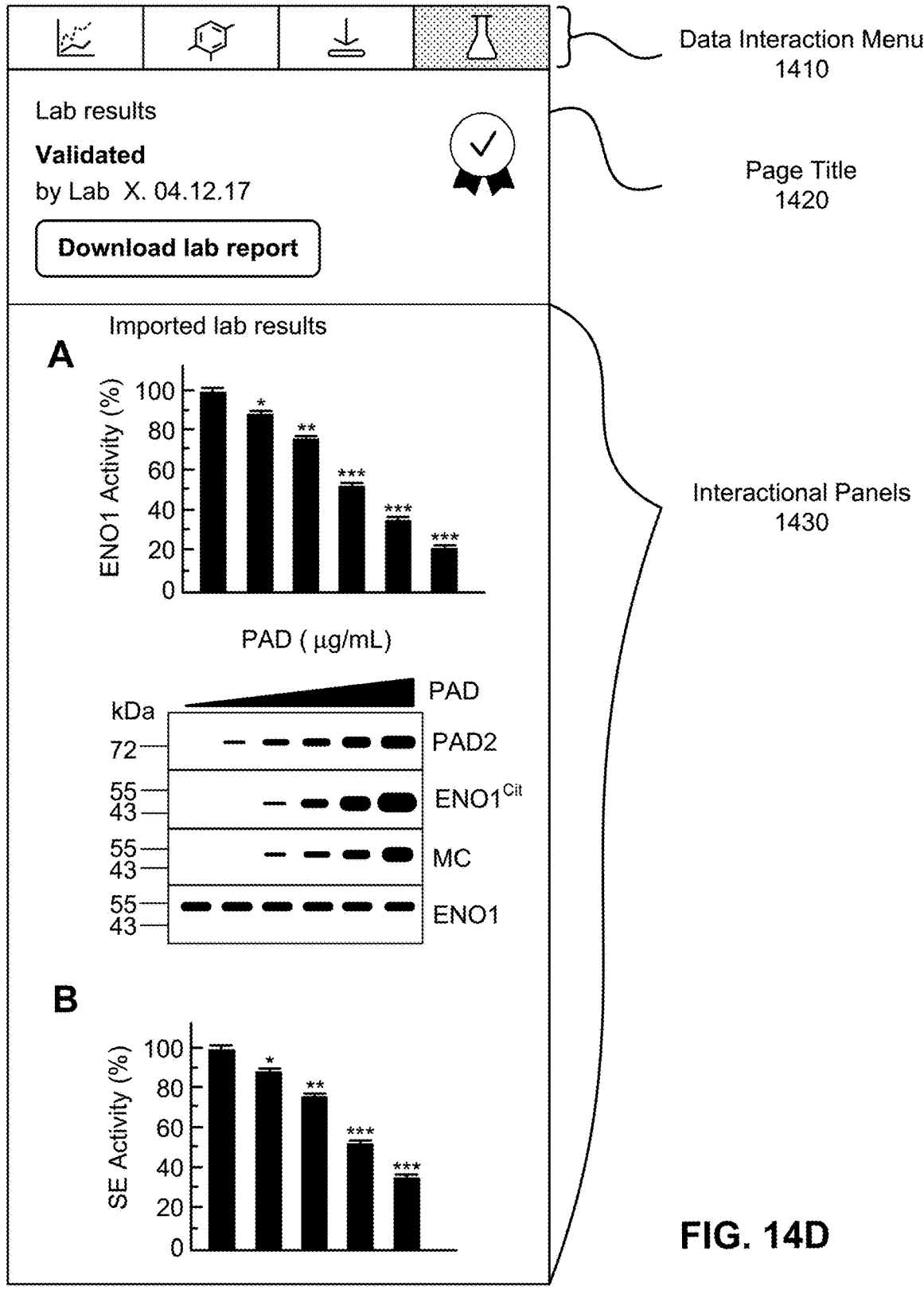

In another embodiment in FIG. 14D, the outcome type bar 930 receives a user input selecting the page for validating the data. In response, the outcome type bar 930 displays the page title 1420 corresponding to that page (e.g. "Validating Dataset"). The interaction panels 1430 then display data from a wetlab simulation or experiment. The user can easily cross reference simulation data with wetlab data.

VI. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method for dynamically generating content through a graphical user interface to be displayed on a display of a computing device comprising:
receiving simulation data corresponding to a biological cell across a plurality of time steps;
displaying a circular viewer comprising a plurality of circular graphical elements in a first portion of the graphical user interface, wherein each circular graphical element represents one biological category of a plurality of biological categories and displays a category of the received simulation data corresponding to the biological category ordered around that circular graphical element;
wherein the plurality of circular graphical elements comprises a first circular graphical element comprising a first category of simulation data corresponding to a first biological category ordered around the first circular graphical element and a second circular graphical element comprising a second category of simulation data corresponding to a second biological category ordered around the second circular graphical element;
receiving an input from a client computing device to adjust display of the circular viewer; and
responsive to the received input to adjust the circular viewer, updating the circular viewer to visually indicate a first subset of simulation data in the first circular graphical element and a second subset of simulation data in the second circular graphical element, wherein the first subset of simulation data and the second subset of simulation data are above a threshold differential from a baseline cell state of the biological cell, wherein the first subset of simulation data and the second subset of simulation data correspond to a first time step of the plurality of time steps.

2. The method of claim 1, wherein a first portion of the first circular graphical element aligns radially with a second portion of the second circular graphical element, wherein the first portion corresponds to simulation data of the first category that is linked to simulation data of the second category.

3. The method of claim 1, further comprising:
responsive to the received input to adjust the circular viewer, updating the circular viewer to visually indicate a third subset of simulation data in the first circular graphical element and a fourth subset of simulation data in the second circular graphical element at a second time step of the plurality of time steps after an interval of time after updating the circular viewer to visually indicate the first subset of simulation data and the second subset of simulation data, wherein the third subset of simulation data and the fourth subset of simulation data are above a threshold differential from a baseline cell state of the biological cell and correspond to the second time step.

4. The method of claim 1, further comprising:
receiving an additional input from the client computing device to adjust display of the circular viewer; and
responsive to the received additional input to adjust the circular viewer, updating the circular viewer to visually indicate a third subset of simulation data in the first circular graphical element and a fourth subset of simulation data in the second circular graphical element, wherein the third subset of simulation data and the fourth subset of simulation data are above a threshold differential from a baseline cell state of the biological cell and correspond to a second time step of the plurality of time steps over which the simulation is run.

5. The method of claim 1, wherein updating the circular viewer to visually indicate the first subset and the second subset comprises any combination of adding an outline, adjusting a coloration, adjusting a saturation, adjusting a hue, shading, geometric scaling, and adding a fill pattern.

6. The method of claim 1, wherein responsive to the received input to adjust the circular viewer further comprises displaying a plurality of indicators representing a plurality of connections between the first subset and the second subset.

7. The method of claim 6, wherein the plurality of indicators are displayed exterior of the plurality of circular graphical elements.

8. The method of claim 1, wherein the first category is DNA replication and the second category is RNA transcription, wherein the ordering of the first category of simulation data in the first circular graphical element and the ordering of the second category of simulation data in the second circular graphical element is based on ordering of DNA in the biological cell.

9. The method of claim 1, wherein the ordering of the first category of simulation data in the first circular graphical element and the ordering of the second category of simulation data in the second circular graphical element is based on an additional received input describing the ordering of the first category of simulation data in the first circular graphical element and the ordering of the second category of simulation data in the second circular graphical element.

10. The method of claim 1, further comprising:
receiving an additional input from the client computing device to select the first subset of simulation data in the first circular graphical element that is visually indicated by the circular viewer; and
responsive to the received additional input to select the first subset of simulation data in the first circular graphical element, updating the circular viewer to further visually distinguish the first subset of simulation data in the first circular graphical element from the second subset of simulation data in the second circular graphical element.

11. The method of claim 1, further comprising:
receiving simulation parameters from the client computing device for a subsequent simulation;
performing the subsequent simulation according to the received simulation parameters, resulting in subsequent simulation data; and
updating the circular viewer with the subsequent simulation data.

12. A computer-readable non-transitory storage medium for dynamically generating content through a graphical user interface to be displayed on a display of a computing device, the storage medium encoded with instructions that, when executed by a processor, cause the processor to:
receive simulation data corresponding to a simulated biological cell across a plurality of time steps;
display a circular viewer comprising a plurality of circular graphical elements in a first portion of the graphical user interface, wherein each circular graphical element represents one biological category of a plurality of biological categories and displays a category of the received simulation data corresponding to the biological category ordered around that circular graphical element;
wherein the plurality of circular graphical elements comprises a first circular graphical element comprising a first category of simulation data corresponding to a first biological category ordered around the first circular graphical element and a second circular graphical element comprising a second category of simulation data corresponding to a second biological category ordered around the second circular graphical element;
receive an input from a client computing device to adjust display of the circular viewer; and
responsive to the received input to adjust the circular viewer, update the circular viewer to visually indicate a first subset of simulation data in the first circular graphical element and a second subset of simulation data in the second circular graphical element, wherein the first subset of simulation data and the second subset of simulation data are above a threshold differential from a baseline cell state of the biological cell,
wherein the first subset of simulation data and the second subset of simulation data correspond to a first time step of the plurality of time steps.

13. The storage medium of claim 12, wherein a first portion of the first circular graphical element aligns radially with a second portion of the second circular graphical element, wherein the first portion corresponds to simulation data of the first category that is linked to simulation data of the second category.

14. The storage medium of claim 12, with further instructions that, when executed by the processor, cause the processor to:
responsive to the received input to adjust the circular viewer, update the circular viewer to visually indicate a third subset of simulation data in the first circular graphical element and a fourth subset of simulation data in the second circular graphical element at a second time step of the plurality of time steps after an interval of time after updating the circular viewer to visually indicate the first subset of simulation data and the second subset of simulation data, wherein the third subset of simulation data and the fourth subset of simulation data are above a threshold differential from a baseline cell state of the biological cell and correspond to the second time step.

15. The storage medium of claim 12, with further instructions that, when executed by the processor, cause the processor to:
receive an additional input from a client computing device to adjust display of the circular viewer; and
responsive to the received additional input to adjust the circular viewer, update the circular viewer to visually indicate a third subset of simulation data in the first circular graphical element and a fourth subset of simulation data in the second circular graphical element, wherein the third subset of simulation data and the fourth subset of simulation data are above a threshold differential from a baseline cell state of the biological cell and correspond to a second time step of the plurality of time steps over which the simulation is run.

16. The storage medium of claim 12, wherein updating the circular viewer to visually indicate the first subset and the second subset comprises any combination of add an outline, adjust a coloration, adjust a saturation, adjust a hue, shading, geometric scaling, and add a fill pattern.

17. The storage medium of claim 12, wherein the first category is DNA replication and the second category is RNA transcription, wherein the ordering of the first category of simulation data in the first circular graphical element and the ordering of the second category of simulation data in the second circular graphical element is based on ordering of DNA in the biological cell.

18. The storage medium of claim 12, wherein the ordering of the first category of simulation data in the first circular graphical element and the ordering of the second category of simulation data in the second circular graphical element is based on an additional received input describing the ordering of the first category of simulation data in the first circular graphical element and the ordering of the second category of simulation data in the second circular graphical element.

\* \* \* \* \*